(12) United States Patent
Izumi et al.

(10) Patent No.: US 9,643,905 B2
(45) Date of Patent: May 9, 2017

(54) PHENYLNAPHTHOL DERIVATIVES

(71) Applicant: TOKUYAMA CORPORATION, Shunan-shi, Yamaguchi (JP)

(72) Inventors: Shinobu Izumi, Shunan (JP); Kazuhiro Teranishi, Shunan (JP)

(73) Assignee: TOKUYAMA CORPORATION, Shunan-shi (JP)

( * ) Notice: Subject to any disclaimer, the term of this patent is extended or adjusted under 35 U.S.C. 154(b) by 0 days.

(21) Appl. No.: 14/896,026

(22) PCT Filed: Jun. 25, 2014

(86) PCT No.: PCT/JP2014/066772
§ 371 (c)(1),
(2) Date: Dec. 4, 2015

(87) PCT Pub. No.: WO2015/002038
PCT Pub. Date: Jan. 8, 2015

(65) Prior Publication Data
US 2016/0130203 A1  May 12, 2016

(30) Foreign Application Priority Data

Jul. 1, 2013 (JP) .................... 2013-137884
Aug. 28, 2013 (JP) .................... 2013-176299

(51) Int. Cl.
| | | |
|---|---|---|
| C07D 311/94 | (2006.01) | |
| C07D 327/04 | (2006.01) | |
| C07D 317/70 | (2006.01) | |
| C07C 43/23 | (2006.01) | |
| C07C 39/23 | (2006.01) | |
| C07C 41/18 | (2006.01) | |

(52) U.S. Cl.
CPC ............. *C07C 39/23* (2013.01); *C07C 41/18* (2013.01); *C07C 43/23* (2013.01); *C07D 311/94* (2013.01); *C07D 317/70* (2013.01); *C07D 327/04* (2013.01); *C07C 2101/16* (2013.01); *C07C 2101/18* (2013.01); *C07C 2103/94* (2013.01)

(58) Field of Classification Search
CPC .. C07D 311/94; C07D 327/04; C07D 317/70; C07C 43/23; C07C 39/23; C07C 41/18
See application file for complete search history.

(56) References Cited

U.S. PATENT DOCUMENTS

| 5,955,520 | A | 9/1999 | Heller et al. |
| 6,296,785 | B1 | 10/2001 | Nelson et al. |
| 2005/0003107 | A1 | 1/2005 | Kumar et al. |
| 2005/0004361 | A1 | 1/2005 | Kumar et al. |
| 2007/0138448 | A1 | 6/2007 | Chopra |
| 2007/0138449 | A1 | 6/2007 | Chopra et al. |
| 2008/0234381 | A1 | 9/2008 | Olesen et al. |
| 2009/0309076 | A1 | 12/2009 | He et al. |
| 2010/0041657 | A1 | 2/2010 | Olesen et al. |
| 2011/0143141 | A1 | 6/2011 | He et al. |
| 2012/0121934 | A1 | 5/2012 | Takahashi et al. |
| 2012/0156508 | A1 | 6/2012 | He et al. |
| 2012/0156521 | A1 | 6/2012 | He et al. |
| 2014/0054520 | A1 | 2/2014 | Takenaka et al. |
| 2014/0154527 | A1 | 6/2014 | Izumi et al. |
| 2014/0225050 | A1 | 8/2014 | Shimizu et al. |

FOREIGN PATENT DOCUMENTS

| CN | 1226267 A | 8/1999 |
| CN | 101175720 A | 5/2008 |

(Continued)

OTHER PUBLICATIONS

Ooi et al., 2007, caplus an 2007:155111.*

(Continued)

*Primary Examiner* — Sun Jae Yoo
(74) *Attorney, Agent, or Firm* — Birch, Stewart, Kolasch & Birch, LLP

(57) ABSTRACT

Phenylnaphthol derivatives represented by the following general formula (1),

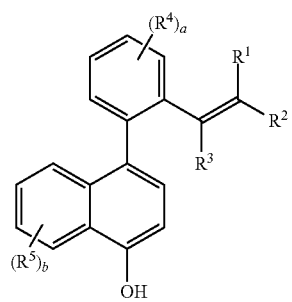

wherein, $R^1$ to $R^3$ are hydrogen atoms, alkyl groups or aryl groups, and $R^2$ and $R^3$ may be bonded together to form an aliphatic hydrocarbon ring or a heterocyclic ring, a and b are, respectively, integers of 0 to 4, $R^4$ and $R^5$ are hydroxyl groups, alkyl groups, haloalkyl groups, cycloalkyl groups, alkoxy groups, amino groups, heterocyclic groups having a nitrogen atom as a hetero atom and are bonded together via the nitrogen atom, cyano groups, nitro groups, formyl groups, hydroxycarbonyl groups, alkylcarbonyl groups, alkoxycarbonyl groups, halogen atoms, aralkyl groups, aralkoxy groups, aryloxy groups, aryl groups, heteroaryl groups bonded together via a carbon atom in the ring, alkylthio groups, cycloalkylthio groups, arylthio groups or heteroarylthio groups, and if $R^4$ or $R^5$ are present in a plural number, the plurality of $R^4$ or the plurality of $R^5$ may be the same or different, or 2 $R^4$s or 2 $R^5$s may be bonded together to form an alicyclic hydrocarbon ring or a heterocyclic ring. The compounds are useful as intermediate products for the synthesis of, for example, photochromic compounds.

2 Claims, No Drawings

(56) References Cited

FOREIGN PATENT DOCUMENTS

| | | |
|---|---|---|
| CN | 101180270 A | 5/2008 |
| CN | 101341141 A | 1/2009 |
| CN | 101346648 A | 1/2009 |
| WO | WO 97/48762 A1 | 12/1997 |
| WO | WO 2006/120178 A1 | 11/2006 |
| WO | WO 2006/125778 A1 | 11/2006 |
| WO | WO 2007/073462 A1 | 6/2007 |
| WO | WO 2007/078529 A1 | 7/2007 |
| WO | WO 2011/016582 A1 | 2/2011 |
| WO | WO 2012/082383 A1 | 6/2012 |
| WO | WO 2012/082506 A1 | 6/2012 |
| WO | WO 2012/082837 A1 | 6/2012 |
| WO | WO 2012/082999 A1 | 6/2012 |
| WO | WO 2012/121414 A1 | 9/2012 |
| WO | WO 2012/176918 A1 | 12/2012 |
| WO | WO 2013/042800 A1 | 3/2013 |

OTHER PUBLICATIONS

Zhang et al. 2014, capus an 2014:531236.*
Xie et al., 2014, caplus an 2014:949038.*
International Search Report, issued in PCT/JP2014/066772, dated Sep. 9, 2014.
Chinese Office Action and Chinese Search Report, issued Aug. 19, 2016, for Chinese Application No. 201480033186.9, along with an English translation of the Chinese Office Action.

* cited by examiner

PHENYLNAPHTHOL DERIVATIVES

TECHNICAL FIELD

This invention relates to novel phenylnaphthol derivatives useful as intermediate products for the production of functional organic materials such as medicines and dyes. More specifically, the invention also relates to a process for producing indenonaphthol compounds and indenonaphthopyrans by using the phenylnaphthol derivatives.

BACKGROUND ART

The phenylnaphthol compound which is a phenylnaphthalene compound is useful as an intermediate product for the production of functional organic materials such as medicines and dyes. For example, the indenonaphthopyran compound which is a photochromic coloring matter is synthesized from the indenonaphthol compound. So far, the indenonaphthol compound has been produced by using a benzophenone compound as a starting material.

According to the conventional method of producing the indenonaphthol compounds from the benzophenone compounds, it was necessary to produce the phenylnaphthol compounds having, on the naphthalene ring thereof, a substituent that is to be converted into an indeno group. Thus, the phenylnaphthol compounds have heretofore been synthesized from the benzophenone compounds through the reactions of a multiplicity of stages. Therefore, the production steps were complex, yields were poor and, as a result, the production cost was high, and improvements have been urged. Specifically, if a benzophenone compound having an asymmetrical molecular structure is used as the starting material, there are formed structural isomers, the phenylnaphthol compound is obtained in a greatly decreased yield, and improvements have been urged (e.g., see patent documents 1 and 2).

If it is attempted to synthesize a benzophenone compound represented by the following formula:

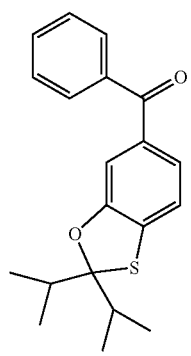 [SMILES: CC(C)C1(C(C)C)Oc2cc(C(=O)c3ccccc3)ccc2S1]

by the Friedel-Craft's acylation reaction, selectivity of the positions to be acylated is so low that it is difficult to obtain the desired product in a high yield. Therefore the benzophenone compound had to be synthesized through a multiplicity of stages without relying on the Friedel-Craft's acylation reaction.

Further, if the indenonaphthol compound is synthesized by using the known phenylnaphthol compound, a severe acidic condition is often required for condensing and cyclizing the naphthalene ring with the indene ring. Therefore, the object product is often decomposed and impurities are, in many cases, by-produced.

Described below is an example of synthesizing the indenonaphthol compound by using the conventional phenylnaphthol compound.

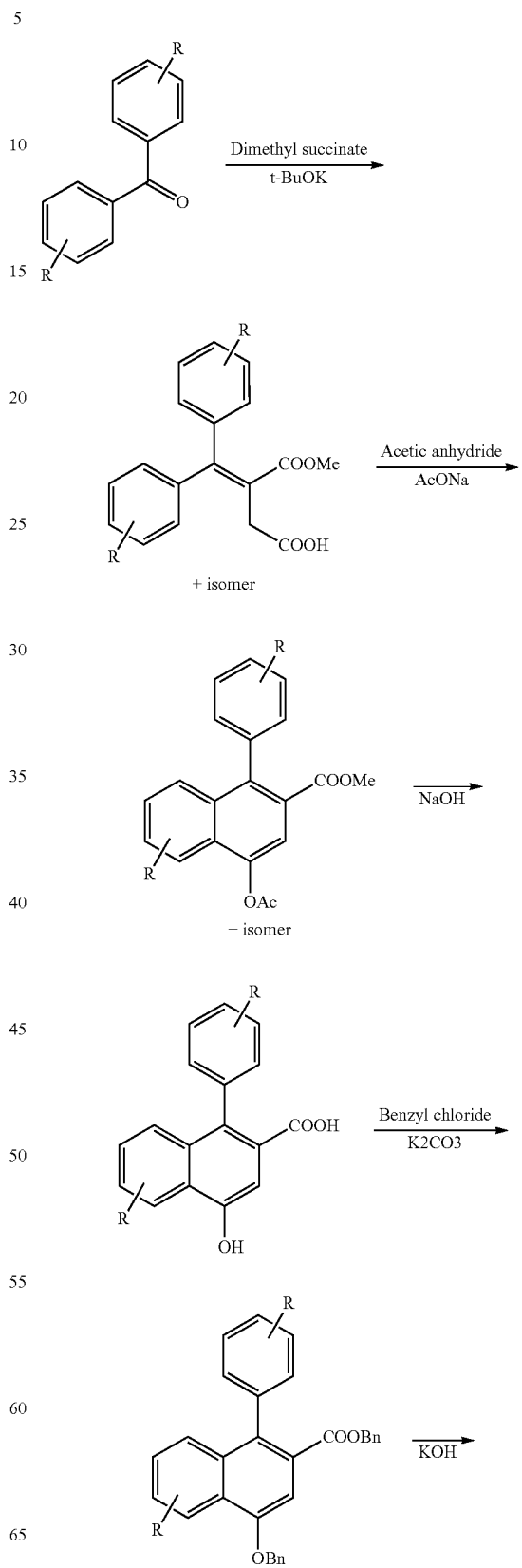

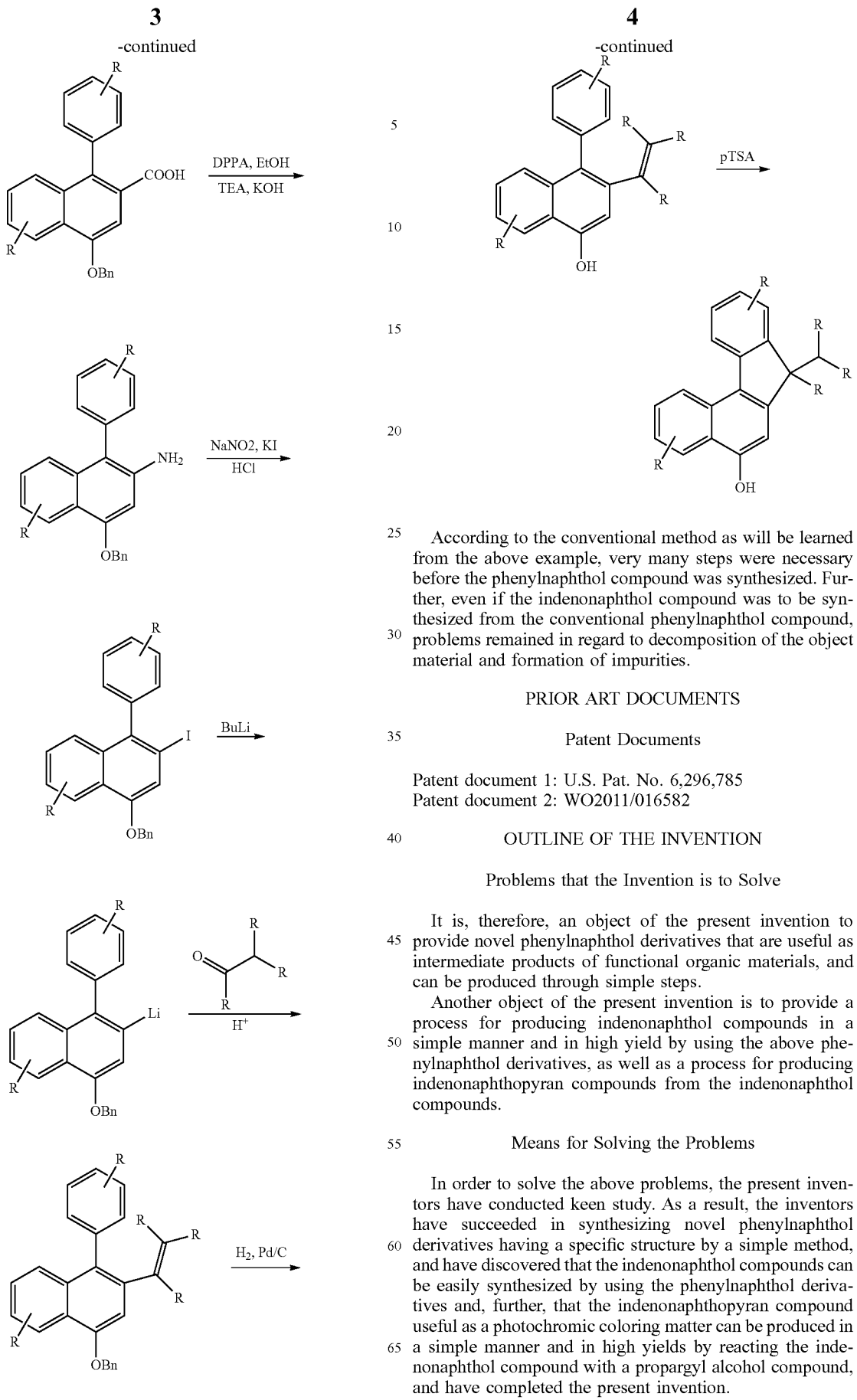

According to the conventional method as will be learned from the above example, very many steps were necessary before the phenylnaphthol compound was synthesized. Further, even if the indenonaphthol compound was to be synthesized from the conventional phenylnaphthol compound, problems remained in regard to decomposition of the object material and formation of impurities.

PRIOR ART DOCUMENTS

Patent Documents

Patent document 1: U.S. Pat. No. 6,296,785
Patent document 2: WO2011/016582

OUTLINE OF THE INVENTION

Problems that the Invention is to Solve

It is, therefore, an object of the present invention to provide novel phenylnaphthol derivatives that are useful as intermediate products of functional organic materials, and can be produced through simple steps.

Another object of the present invention is to provide a process for producing indenonaphthol compounds in a simple manner and in high yield by using the above phenylnaphthol derivatives, as well as a process for producing indenonaphthopyran compounds from the indenonaphthol compounds.

Means for Solving the Problems

In order to solve the above problems, the present inventors have conducted keen study. As a result, the inventors have succeeded in synthesizing novel phenylnaphthol derivatives having a specific structure by a simple method, and have discovered that the indenonaphthol compounds can be easily synthesized by using the phenylnaphthol derivatives and, further, that the indenonaphthopyran compound useful as a photochromic coloring matter can be produced in a simple manner and in high yields by reacting the indenonaphthol compound with a propargyl alcohol compound, and have completed the present invention.

Namely, according to the present invention, there are provided phenylnaphthol derivatives represented by the following general formula (1):

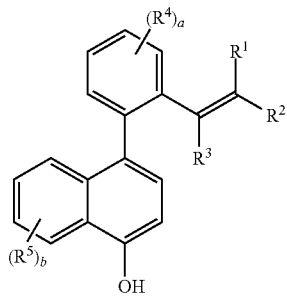

(1)

wherein, $R^1$, $R^2$ and $R^3$ are hydrogen atoms, alkyl groups or aryl groups, and $R^2$ and $R^3$ may be bonded together to form an aliphatic hydrocarbon ring or a heterocyclic ring, a is an integer of 0 to 4, b is an integer of 0 to 4, $R^4$ and $R^5$ are hydroxyl groups, alkyl groups, haloalkyl groups, cycloalkyl groups, alkoxy groups, amino groups, heterocyclic groups having a nitrogen atom as a hetero atom and are bonded together via the nitrogen atom, cyano groups, nitro groups, formyl groups, hydroxycarbonyl groups, alkylcarbonyl groups, alkoxycarbonyl groups, halogen atoms, aralkyl groups, aralkoxy groups, aryloxy groups, aryl groups, heteroaryl groups bonded together via a carbon atom in the ring, alkylthio groups, cycloalkylthio groups, arylthio groups or heteroarylthio groups, and if $R^4$ or $R^5$ are present in a plural number, the plurality of $R^4$ or the plurality of $R^5$ may be the same or different, or 2 $R^4$s or 2 $R^5$s may be bonded together to form an alicyclic hydrocarbon ring or a heterocyclic ring.

According to the present invention, further, there is provided a process for producing an indenonaphthol compound represented by the following formula (2):

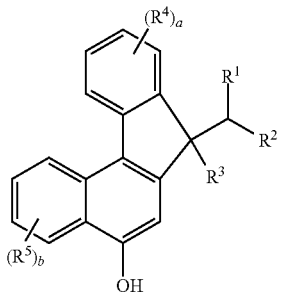

(2)

wherein $R^1$, $R^2$, $R^3$, $R^4$, $R^5$, a and b are as defined in the formula (1), by cyclizing the above phenylnaphthol derivative in the presence of an acid catalyst.

According to the present invention, further, there is provided a process for producing an indenonaphthopyran compound represented by the following general formula (3):

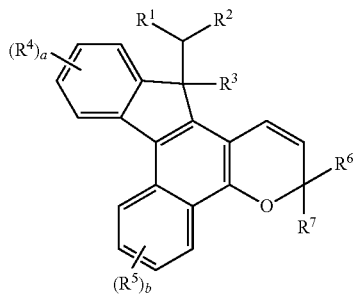

(3)

wherein $R^1$, $R^2$, $R^3$, $R^4$, $R^5$, a and b are as defined in the formula (1), and $R^6$ and $R^7$ are alkyl groups, cycloalkyl groups, aryl groups or heteroaryl groups, by reacting the indenonaphthol compound produced by the above method with a propargyl alcohol compound represented by the following general formula (4):

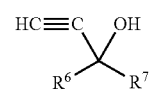

(4)

wherein $R^6$ and $R^7$ are as defined in the above formula (3).

In the invention, further, among the phenylnaphthol derivatives of the above-mentioned general formula (1), a compound having a structure in which the plurality of $R^5$s are bonded together to form a heterocyclic ring or, concretely, a phenylnaphthol derivative represented by the following general formula (1″) can be produced by reacting a halogenonaphthol derivative represented by the following general formula (1-1a) with a boron-containing phenyl compound represented by the following general formula (1-2).

General formula (1″):

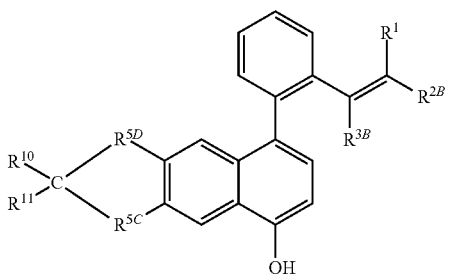

(1″)

wherein, $R^1$ is a hydrogen atom, an alkyl group or an aryl group, $R^{10}$ and $R^{11}$ are hydrogen atoms, alkyl groups, cycloalkyl groups or aryl groups, $R^{2B}$ and $R^{3B}$ are groups which, upon being bonded together, form an aliphatic hydrocarbon ring or a heterocyclic ring, and $R^{5C}$ and $R^{5D}$ are oxygen atoms or sulfur atoms provided either one of them is a sulfur atom.

General formula (1-1a):

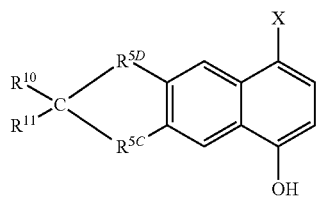

(1-1a)

wherein X is a halogen atom, and
$R^{10}$, $R^{11}$, $R^{5C}$ and $R^{5D}$ are as defined in the above general formula (1").

General formula (1-2):

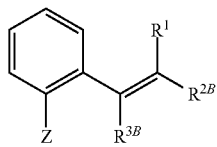

(1-2)

wherein $R^1$ is a hydrogen atom, an alkyl group or an aryl group, $R^{2B}$ and $R^{3B}$ are as defined in the above general formula (1"), and
a group represented by Z is a boron-containing group selected from the following formulas:

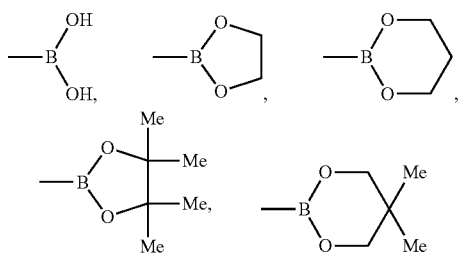

In the invention, the halogenonaphthol derivatives represented by the above formula (1-1a) are produced by halogenating the naphthol derivatives represented by the following general formula (1-1b):

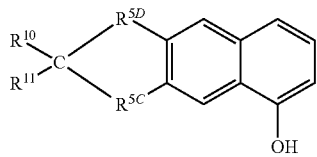

(1-1b)

wherein $R^{5C}$, $R^{5D}$, $R^{10}$ and $R^{11}$ are as defined in the above general formula (1-1a),
in a solvent that contains acetonitrile and/or toluene.

In the invention, further, the halogenonaphthol derivatives represented by the above general formula (1-1a) and the naphthol derivatives represented by the general formula (1-1b) are all novel compounds.

Effects of the Invention

By using the phenylnaphthol derivatives of the invention as starting materials, it is allowed to produce indenonaphthol compounds more simply and in higher yields than by the conventional processes.

Further, by reacting the indenonaphthol compound with the propargyl alcohol compound, it is also allowed to produce the indenonaphthopyran derivatives that are useful as photochromic coloring matters.

MODES FOR CARRYING OUT THE INVENTION

<Phenylnaphthol Derivatives>
The phenylnaphthol derivatives of the present invention are represented by the following general formula (1).

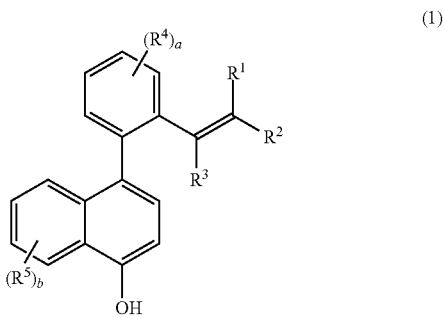

(1)

If the phenylnaphthol derivatives are to be used for the production of indenonaphthol derivatives that will be described later, a protection group can be introduced into the OH group in a customary manner.

If the protection group is denoted by Ra, then —OH in the general formula (1) becomes —ORa. In every reaction, therefore, the reaction with the OH group is prevented and formation of by-products is suppressed.

The protection group Ra for the OH group has been known per se. as represented by alkyl protection group, acetal protection group, benzyl protection group and silyl protection group. As the alkyl protection group, a methyl group is preferred.

As the acetal protection group, there can be preferably used a methoxymethyl group, a methoxyethoxymethyl group or a tetrahydropyranyl group.

As the benzyl protection group, a benzyl group and a p-methoxybenzyl group are preferred.

As the silyl protection group, there is preferably used a trimethylsilyl group, a triethylsilyl group, a triisopropylsilyl group or a t-butyldimethylsilyl group.

In the phenylnaphthol derivatives of the invention, particularly preferred protection groups are methyl group, benzyl group, methoxymethyl group, methoxyethyl group, tetrahydropyranyl group and trimethylsilyl group.

The protection group Ra for the hydroxyl group can be suitably introduced into any compounds not being limited to only the phenylnaphthol derivatives of the invention represented by the general formula (1).

(Groups $R^1$, $R^2$ and $R^3$)

$R^1$, $R^2$ and $R^3$ in the above general formula (1) are, respectively, hydrogen atoms, alkyl groups or aryl groups.

The alkyl group, desirably, has 1 to 6 carbon atoms, and its preferred examples are methyl group, ethyl group, n-propyl group, isopropyl group, n-butyl group, sec-butyl group, tert-butyl group, pentyl group, hexyl group and the like groups.

The aryl group, desirably, has 6 to 14 carbon atoms, and its preferred examples are phenyl group, 1-naphthyl group, 2-naphthyl group and the like groups.

Further, the aromatic ring possessed by the aryl group may have 1 to 4 and, specifically, 1 to 2 substituents (e.g., the above-mentioned alkyl groups or alkoxy groups).

Further, $R^2$ and $R^3$ may be bonded together to form an aliphatic hydrocarbon or a heterocyclic ring that has at least one of oxygen atom, sulfur atom or nitrogen atom as a hetero atom. The number of atoms that constitute the ring is, usually, in a range of 4 to 20 and, specifically, 5 to 12. The above alkyl group or the aryl group may be possessed as the substituent.

Among the phenylnaphthol derivatives in which $R^2$ and $R^3$ are bonded together to form an aliphatic hydrocarbon ring or a heterocyclic ring, preferred are the compounds represented by the following formulas from such a standpoint that the indenonaphthopyran compounds finally synthesized from these compounds exhibit excellent photochromic properties.

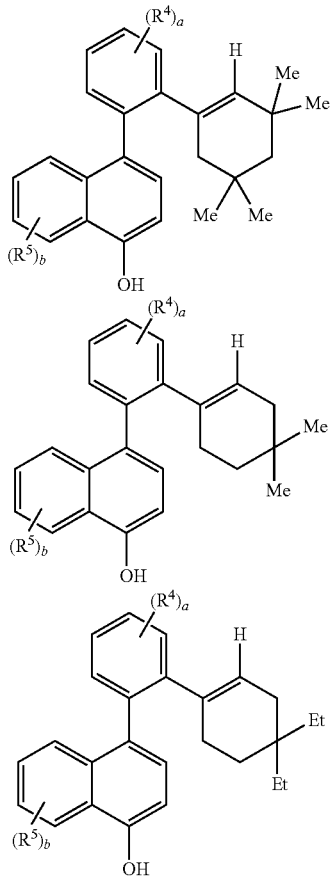

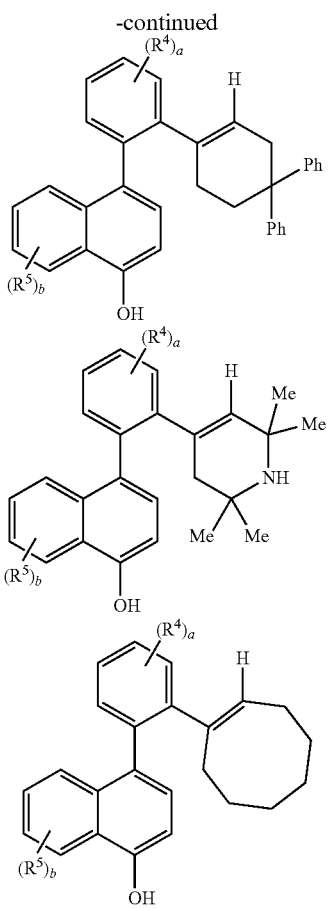

(a, b, and Groups $R^4$ and $R^5$)

In the above general formula (1), a denotes the number of the groups $R^4$s and is an integer of 0 to 4. Further, b denotes the number of the groups $R^5$s and is an integer of 0 to 4.

$R^4$ and $R^5$ are, respectively, hydroxyl groups, alkyl groups, haloalkyl groups, cycloalkyl groups, alkoxy groups, amino groups, heterocyclic groups having a nitrogen atom as a hetero atom and bonded together via the nitrogen atom, cyano groups, nitro groups, formyl groups, hydroxycarbonyl groups, alkylcarbonyl groups, alkoxycarbonyl groups, halogen atoms, aralkyl groups, aralkoxy groups, aryloxy groups, aryl groups, heteroaryl groups bonded together via a carbon atom in the ring, alkylthio groups, cycloalkylthio groups, arylthio groups or heteroarylthio groups.

If $R^4$s or $R^5$s are present in a plural number (a or b is an integer of 2 to 4), the plurality of these groups ($R^4$s or $R^5$s) may be the same or different from each other.

As the above alkyl group and aryl group, there can be exemplified the same groups as those described above concerning $R^1$.

The haloalkyl group is, desirably, an alkyl group having 1 to 6 carbon atoms and having, as a substituent, a fluorine atom, a chlorine atom or a bromine atom, and is, specifically, a trifluoromethyl group, tetrafluoroethyl group, chloromethyl group, 2-chloroethyl group or bromomethyl group.

The cycloalkyl group has, desirably, 3 to 8 carbon atoms, and is, specifically, a cyclopropyl group, cyclobutyl group, cyclopentyl group or cyclohexyl group.

The alkoxy group has, desirably, 1 to 6 carbon atoms, and is, specifically, a methoxy group, ethoxy group, n-propoxy group, isopropoxy group, n-butoxy group, sec-butoxy group or tert-butoxy group.

The amino group is not limited to a primary amino group (—NH$_2$) but may be a secondary or a tertiary amino group in which 1 or 2 hydrogen atoms have been substituted. As the substituent possessed by the amino group, there can be exemplified an alkyl group having 1 to 6 carbon atoms, haloalkyl group having 1 to 6 carbon atoms, alkoxy group having 1 to 6 carbon atoms, cycloalkyl group having 3 to 7 carbon atoms, aryl group having 6 to 14 carbon atoms, and heteroaryl group having 4 to 14 carbon atoms.

Particularly preferred examples of the amino group are primary amino group, methylamino group, dimethylamino group, ethylamino group, diethylamino group, phenylamino group and diphenylamino group.

The heterocyclic group is not specifically limited if it has a nitrogen atom as a hetero atom and is bonded via the nitrogen atom, and may, for example, be the one of the aliphatic type or the aromatic type. Its concrete examples include morpholino group, piperidino group, pyrrolidinyl group, piperadino group and N-methylpiperadino group. Further, the heterocyclic groups may have a substituent such as alkyl group. Preferred examples of the heterocyclic group having such substituents include 2,6-dimethylmorpholino group, 2,6-dimethylpiperidino group and 2,2,6,6-tetramethylpiperidino group.

The alkalicarbonyl group has, desirably, 2 to 7 carbon atoms, and is, specifically, acetyl group or ethylcarbonyl group.

The alkoxycarbonyl group has 2 to 7 carbon atoms, and is, preferably methoxycarbonyl group or ethoxycarbonyl group.

As the halogen atom, there can be exemplified fluorine atom, chlorine atom, bromine atom and iodine atom.

As the aralkyl group, there can be exemplified those having 7 to 11 carbon atoms, such as benzyl group, phenylethyl group, phenylpropyl group, phenylbutyl group and naphthylmethyl group.

As the aralkoxy group, there can be exemplified those having 7 to 11 carbon atoms, such as benzyloxy group and naphthylmethoxy group.

As the aryloxy group, an aryloxy group having 6 to 12 carbon atoms is preferred. Preferred examples of the aryloxy group include phenyloxy group and naphthyloxy group.

The aryl group, desirably, has 6 to 14 carbon atoms. Preferred examples of the aryl group include phenyl group, 1-naphthyl group and 2-naphthyl group.

The above aralkyl group, aralkoxy group, aryloxy group and aryl group may have not more than 7 and, specifically, not more than 4 substituents bonded to the aromatic ring thereof. As the substituent, there can be exemplified the above-mentioned hydroxyl group, alkyl group, haloalkyl group, cycloalkyl group, alkoxy group, amino group, heterocyclic group having a nitrogen atom as a hetero atom and is bonded via the nitrogen atom, cyano group, nitro group and halogen atom.

The heteroaryl group is bonded via a carbon atom in the ring. As the heterocyclic ring possessed by this group, though there is no specific limitation, there can be preferably used a 5-to 7-membered aromatic heterocyclic ring having 1 to 2 hetero atoms (oxygen atoms, nitrogen atoms or sulfur atoms), or a condensed ring of the aromatic heterocyclic ring and a benzene ring. Particularly preferred examples of the heteroaryl group include thienyl group, furyl group, pyrrolinyl group, piridyl group, benzothienyl group, benzofuranyl group and benzopyrrolinyl group.

The heteroaryl group may have 1 to 6 and, specifically, 1 to 4 substituents bonded to the aromatic heterocyclic ring thereof. As the substituent, there can be exemplified the above-mentioned hydroxyl group, alkyl group, haloalkyl group, cycloalkyl group, alkoxy group, amino group, heterocyclic group having a nitrogen atom as a hetero atom and is bonded via the nitrogen atom, cyano group, nitro group and halogen atom.

As the alkylthio groups, preferred examples include those having 1 to 6 carbon atoms, such as methylthio group, ethylthio group, n-propylthio group, isopropylthio group, n-butylthio group, sec-butylthio group and t-butylthio group.

As the cycloalkylthio groups, preferred examples include those having 3 to 8 carbon atoms, such as cyclopropylthio group, cyclobutylthio group, cyclopentylthio group and cyclohexylthio group.

As the arylthio group, preferred examples include those having 6 to 10 carbon atoms, such as phenylthio group, 1-naphthylthio group and 2-naphthylthio group.

As the heteroarylthio group, preferred examples include those having 4 to 12 carbon atoms, such as thienylthio group, furylthio group, pyrrolylthio group, pyridylthio group, benzothienylthio group, benzofurylthio group and benzopyrrolylthio group.

Further, the above arylthio group and the heteroarylthio group may have 1 to 5 and specifically, 1 to 4 substituents in the aromatic ring thereof. As the substituent, there can be exemplified alkyl group having 1 to 6 carbon atoms, alkoxy group having 1 to 6 carbon atoms, cycloalkyl group having 3 to 8 carbon atoms, and halogen atom.

In the above general formula (1), if $R^4$s or $R^5$s are present in a plural number (i.e., a or b is 1 to 4), two $R^4$s or $R^5$s may be bonded together to form an aliphatic hydrocarbon ring or a heterocyclic ring having an oxygen atom, sulfur atom or nitrogen atom as a hetero atom. The aliphatic hydrocarbon ring or the heterocyclic ring, usually, has atoms in a number in a range of 4 to 8 and, specifically, 5 to 6 to constitute the ring.

In the invention, among the phenylnaphthol derivatives in which two $R^4$s and $R^5$s are bonded together to form an aliphatic hydrocarbon ring or a heterocyclic ring, preferred are the compounds represented by the following formulas from such a standpoint that the indenonaphthopyran compounds finally synthesized from these compounds exhibit excellent photochromic properties.

Embodiments in which two $R^4$s are bonded together to form a ring;

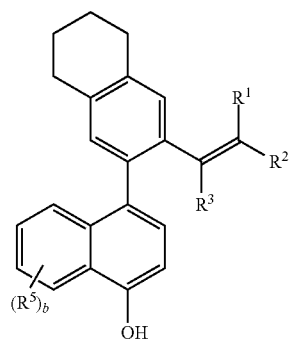

-continued
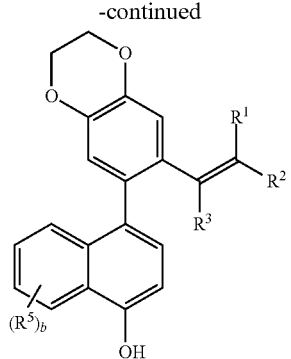
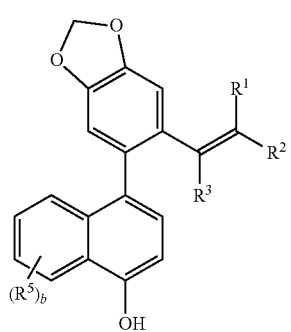
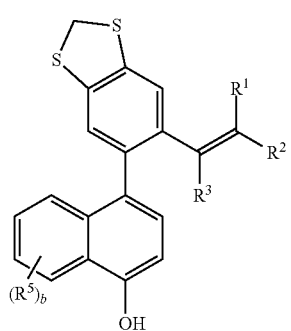
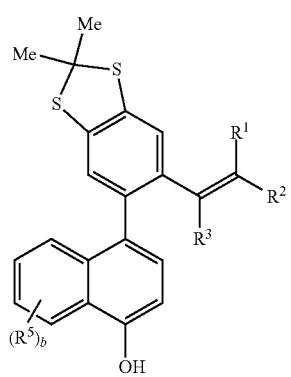
Embodiments in which two R⁵s are bonded together to form a ring;
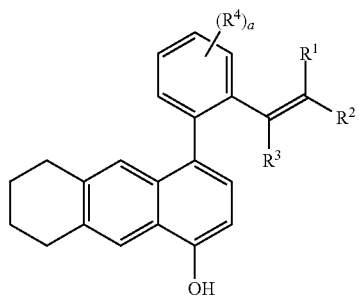
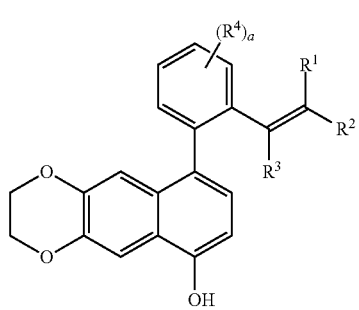
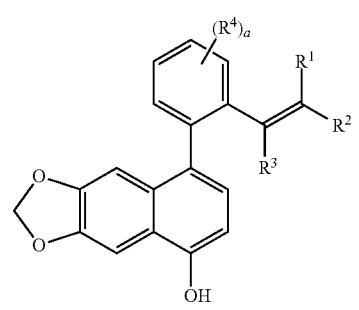
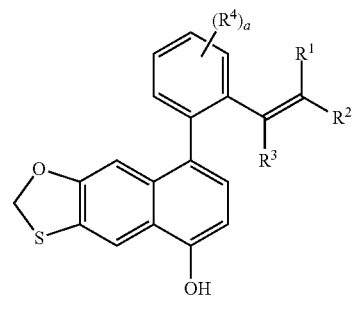
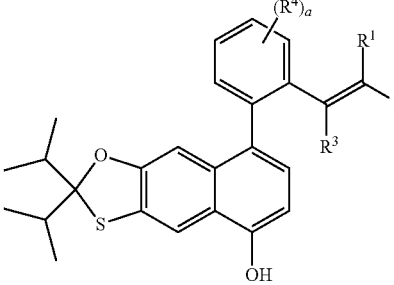

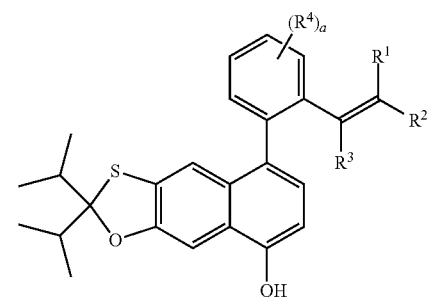

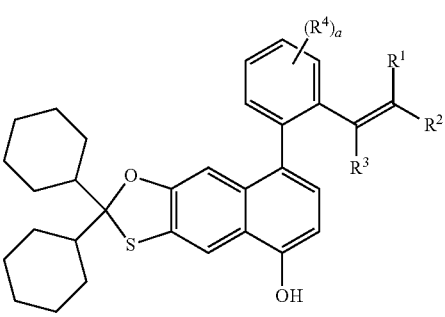

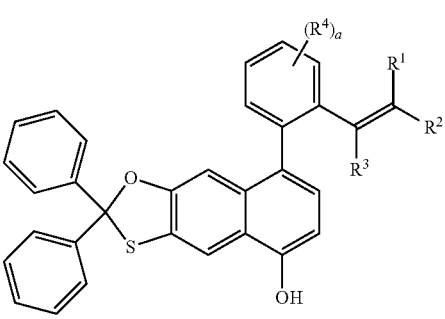

(Preferred Phenylnaphthol Derivatives)

In the phenylnaphthol derivatives of the present invention represented by the above general formula (1), particularly preferred groups in the general formula (1) are as described below from such a standpoint that the indenonaphthopyran compounds synthesized from these derivatives exhibit excellent photochromic properties.

For instance, $R^1$ is, preferably, a hydrogen atom or an alkyl group.

It is, further, desired that $R^2$ and $R^3$ are bonded together to form an aliphatic hydrocarbon ring.

$R^4$ is, preferably, an alkyl group, an alkoxy group or a heterocyclic group having a nitrogen atom as a hetero atom and is bonded via the nitrogen atom, or is also, preferably, an aliphatic hydrocarbon ring or a heterocyclic ring formed by the two $R^4$s that are bonded together.

$R^5$ is, preferably, an alkyl group, alkoxy group, aryloxy group, aryl group, alkylthio group, cycloalkylthio group, arylthio group or heterocyclic group having a nitrogen atom as a hetero atom and is bonded via the nitrogen atom, or is also, preferably, an aliphatic hydrocarbon ring or a heterocyclic ring formed by the two $R^5$s that are bonded together.

The above preferred phenylnaphthol derivatives are represented by the following formula (1').

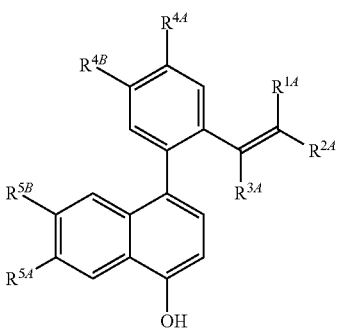

(1')

In the above general formula (1'), $R^{1A}$ corresponds to $R^1$ in the general formula (1) and is a hydrogen atom or an alkyl group, $R^{2A}$ and $R^{3A}$ correspond to $R^2$ and $R^3$ in the general formula (1) and are bonded together to form an aliphatic hydrocarbon ring, $R^{4A}$ and $R^{4B}$ correspond to $R^4$ in the general formula (1) and are, respectively, hydrogen atoms, alkyl groups, alkoxy groups or heterocyclic groups having a nitrogen atom as a hetero atom and are bonded via the nitrogen atom, wherein $R^{4A}$ and $R^{4B}$ may be bonded together to form an aliphatic hydrocarbon ring or a heterocyclic ring, and $R^{5A}$ and $R^{5B}$ correspond to $R^4$ in the general formula (1) and are, respectively, hydrogen atoms, alkyl groups, alkoxy groups, aryloxy groups, aryl groups, alkylthio groups, cycloalkylthio groups, arylthio groups or heterocyclic groups having a nitrogen atom as a hetero atom and are bonded via the nitrogen atom, wherein $R^{4A}$ and $R^{4B}$ may be bonded together to form an aliphatic hydrocarbon ring or a heterocyclic ring.

In the invention, the following compounds can be exemplified as the particularly preferred phenylnaphthol derivatives.

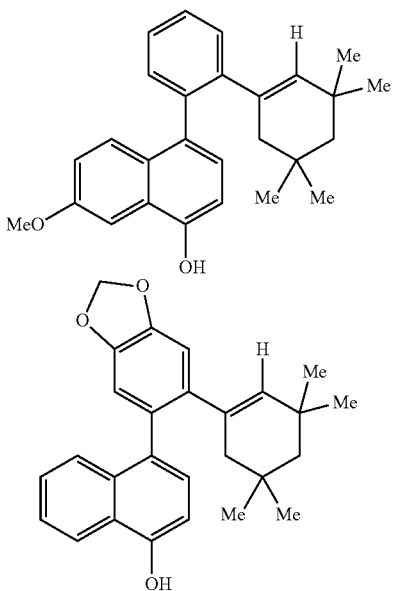

-continued

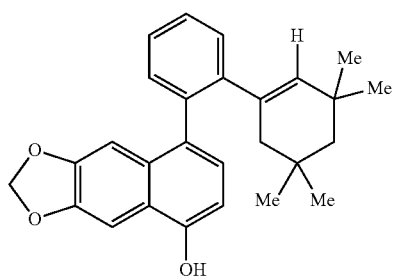

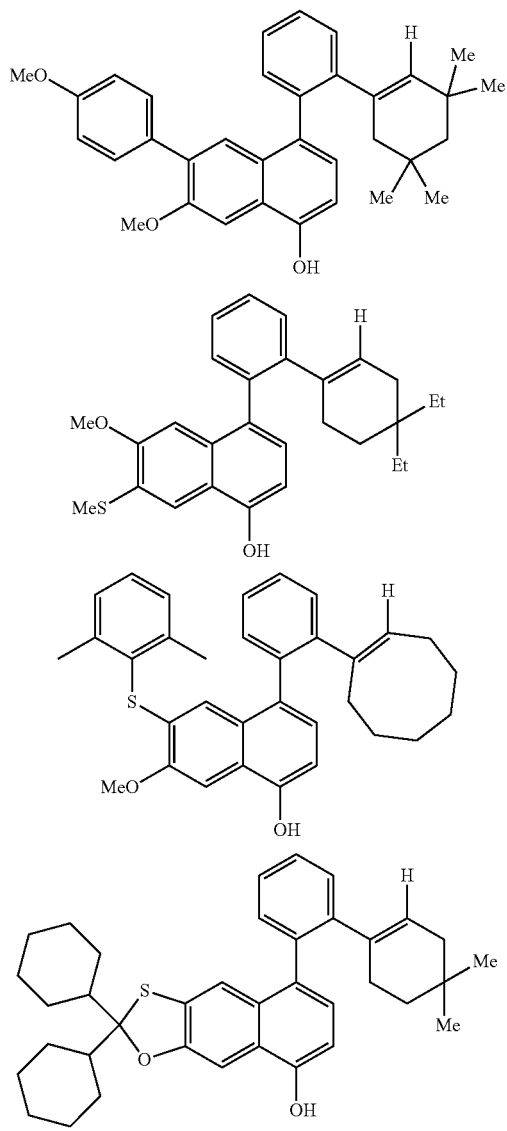

-continued

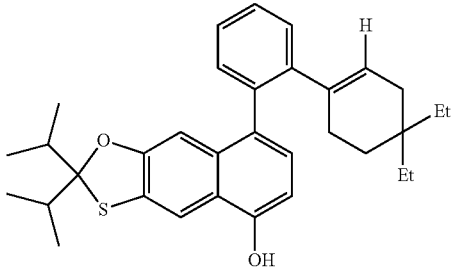

<Production of the Phenylnaphthol Derivatives>

The phenylnaphthol derivatives of the invention represented by the above general formula (1) can be produced by any one of the following synthesizing methods (A) to (C) based on the Suzuki-Miyaura coupling reaction by using, as the starting material, the halogenonaphthol compound represented by the following general formula (1-1);

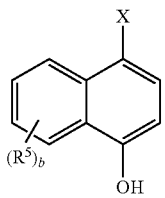
(1-1)

wherein,
X is a halogen atom and is, preferably, a chlorine atom, a bromine atom or an iodine atom, and
$R^5$ and b are as defined in the above general formula (1), and, as required, introducing the protection group Ra into the OH group of the compound.

(Synthesizing Method A)

In the synthesizing method A, the desired phenylnaphthol derivatives are produced through the following reaction path.

In the following reaction path, the protection group Ra has been introduced into the starting material.

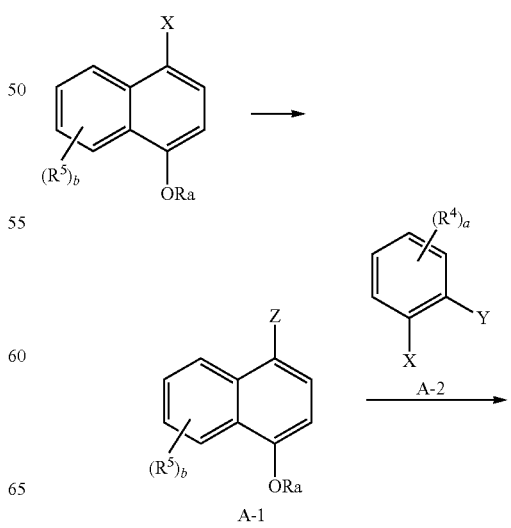

-continued

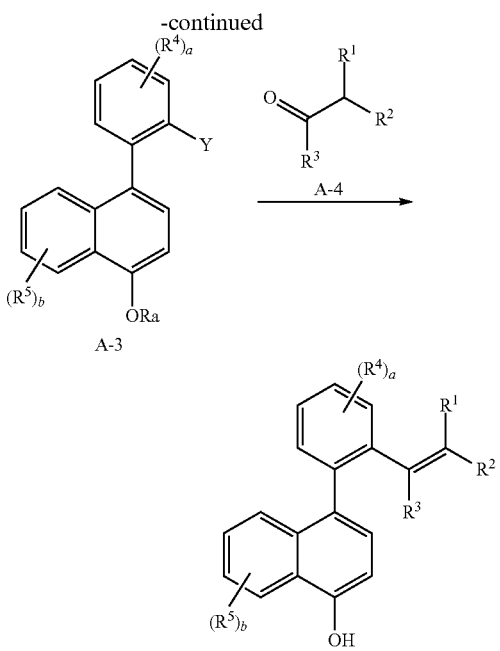

In the above reaction path and in the reaction paths of the synthesizing methods (B) and (C) that will be described later, Y is a halogen atom and is, preferably, a chlorine atom, a bromine atom or an iodine atom, and other groups $R^1$ to $R^5$, a and b are as defined in the general formula (1).

Further, Z is a boron-containing group, such as boronic acid group or boronic acid ester group represented by the following formulas;

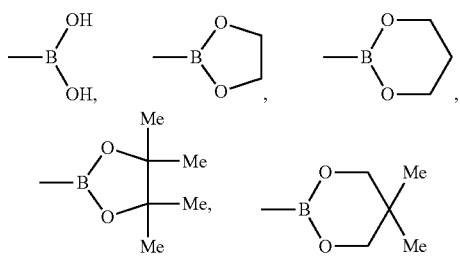

That is, in the synthesizing method A, a halogeno group X of the halogenonaphthol compound of the general formula (1-1) which is the starting compound is converted into a boronic acid or a boronic acid ester (converted into a group Z) after the protection group Ra has been suitably introduced into the hydroxyl group to thereby synthesize a boron-containing naphthol compound (A-1).

The boron-containing naphthol compound (A-1) is then reacted with a phenyl compound (A-2) relying on the Suzuki-Miyaura coupling by using a palladium catalyst or a nickel catalyst to thereby obtain a phenylnaphthol (A-3) which is an intermediate product.

Thereafter, the phenylnaphthol (A-3) is reacted with magnesium or an organolithium compound to effect halogen-metal exchange followed by the reaction with a carbonyl compound (A-4). The tertiary alcohol that is formed is dehydrated with an acid and, as required, the protection group of the hydroxyl group is removed from the obtained compound to thereby obtain a desired phenylnaphthol derivative of the general formula (1).

Through the above reaction path, a compound is obtained in which the halogen atom X of the halogenonaphthol compound of the general formula (1-1) has been converted into the boronic acid or the boronic acid ester. The halogeno group can be converted into the boronic acid or the boronic acid ester by a known method. For instance, the halogeno group is reacted with an organolithium compound and is, thereafter, reacted with a boric ester compound such as trimethyl borate or triisopropyl borate followed by the treatment with an acid to thereby obtain a corresponding boronic acid.

The Suzuki-Miyaura coupling, too, can be effected according to a known method.

As the reaction solvent, for example, there is used an N,N-dimethylformamide, N,N-dimethylsulphoxide, benzene, toluene, xylene, methanol, ethanol, 2-propanol, tetrahydrofuran, or 1,2-dimethoxyethane.

As the palladium catalyst, further, there can be used such a palladium catalyst as tetrakistriphenylphosphine palladium, [1,1-bis(diphenylphosphino)ferrocene]dichloropalladium or tris(dibenzylideneacetone)dipalladium, or such a nickel catalyst as bis(triphenylphosphine)nickel dichloride, or dichloro [1,2-bis(diphenylphosphino)ethane]nickel.

Further, as the base to be made present in the reaction, there is used sodium carbonate, potassium carbonate, cesium carbonate, sodium hydroxide, potassium hydroxide, sodium acetate or potassium acetate.

The reaction temperature is, preferably, 30 to 150° C.

The product formed by the Suzuki-Miyaura coupling can be refined by, for example, the column chromatography using silica gel or by the recrystallization.

The halogen-metal exchange reaction in the above reaction path is effected in a solvent such as benzene, toluene, tetrahydrofuran, diethyl ether, dibutyl ether or t-butyl methyl ether. Further, the organolithium compound used in the reaction can be represented by n-butyl lithium, sec-butyl lithium and t-butyl lithium.

(Synthesizing Method B)

In the synthesizing method B, the desired phenylnaphthol derivatives are produced through the following reaction path.

In the following reaction path, the protection group Ra has been introduced into the starting material.

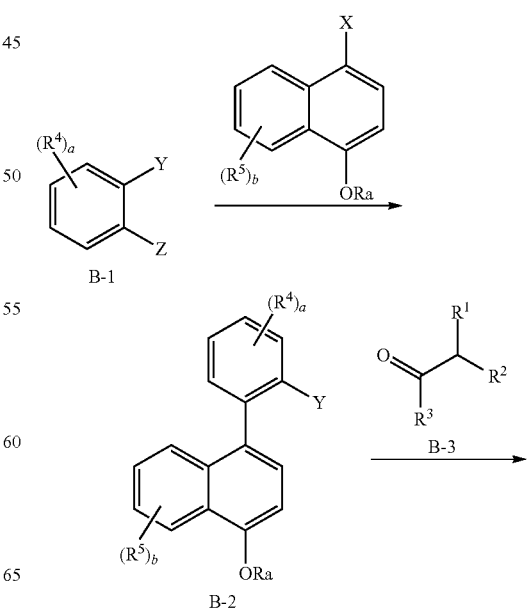

-continued

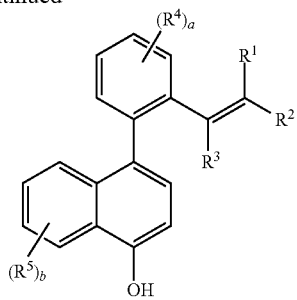

In the synthesizing method B, after a suitable protection group Ra is introduced into the OH group of the halogenonaphthol compound which is the starting material, the boron-containing phenyl compound (B-1) is reacted relying on the Suzuki-Miyaura coupling in the same manner as described above to thereby obtain a phenylnaphthol (B-2).

Thereafter, in the same manner as in the above synthesizing method (A), the phenylnaphthol (B-2) is reacted with magnesium or an organolithium compound to effect halogen-metal exchange followed by the reaction with a carbonyl compound (B-3). The tertiary alcohol that is formed is dehydrated with an acid and, as required, the protection group of the hydroxyl group is removed from the obtained compound to thereby obtain a desired phenylnaphthol derivative of the general formula (1).

(Synthesizing Method C)

In the synthesizing method C, the desired phenylnaphthol derivatives are produced through the following reaction path.

In the following reaction path, too, the protection group Ra has been introduced into the starting material.

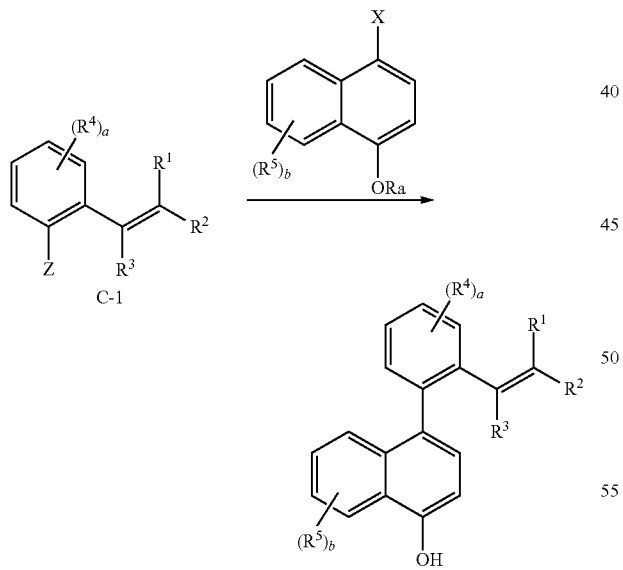

In the synthesizing method C, after a suitable protection group Ra is introduced into the OH group of the halogenonaphthol compound which is the starting material, the boron-containing phenyl compound (C-1) is reacted relying on the Suzuki-Miyaura coupling in the same manner as described above and, as required, the protection group Ra of the hydroxyl group is removed to thereby obtain the phenylnaphthol derivative of the present invention.

As described above, the phenylnaphthol derivatives of the present invention can be synthesized by any one of the above-mentioned synthesizing methods A to C. To put the invention into practice on an industrial scale, therefore, any one of the above synthesizing methods A to C may be selected by taking into consideration the availability of the starting materials and easiness of synthesis.

<Starting Compounds and Their Production>

As described above, the phenylnaphthol derivatives of the present invention can be synthesized by using the halogenonaphthol compounds represented by the general formula (1-1) as the starting material. Among these halogenonaphthol compounds, however, the halogenonaphthol derivatives represented by the following general formula (1-1a):

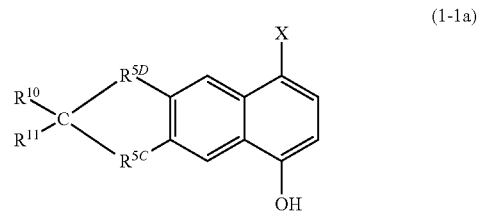

(1-1a)

wherein,

X is a halogen atom, $R^{5C}$ and $R^{5D}$ are oxygen atoms or sulfur atoms provided either one of them is the sulfur atom, and $R^{10}$ and $R^{11}$ are, respectively, hydrogen atoms, alkyl groups, cycloalkyl groups or aryl groups, are novel compounds. That is, upon using the halogenonaphthol derivatives as the starting material, it is allowed to synthesize the phenylnaphthol derivatives in which the two groups $R^5$ in the above general formula (1) are bonded together to form a heterocyclic ring.

These halogenonaphthol derivatives can be synthesized by using the naphthol compound represented by the following formula:

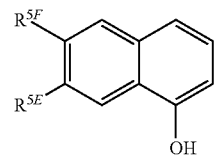

wherein, $R^{5E}$ and $R^{5F}$ are hydroxyl groups or thiol groups provided either one of them is the thiol group.

That is, the above naphthol compound is thioacetalized by using a ketone compound represented by the following formula:

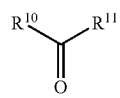

wherein $R^{10}$ and $R^{11}$ are as defined in the above general formula (1-1a), to obtain the naphthol derivatives represented by the following formula (1-1b):

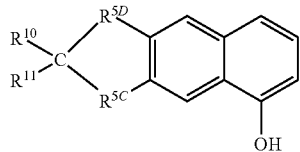
(1-1b)

wherein $R^{5C}$, $R^{5D}$, $R^{10}$ and $R^{11}$ are as defined in the above general formula (1-1a).

The naphthol derivatives are halogenated to synthesize the halogenonaphthol derivatives represented by the general formula (1-1a).

In synthesizing the halogenonaphthol derivatives as described above, the above-mentioned protection group may have been suitably introduced into the hydroxyl group that is bonded to the naphthalene ring.

The thioacetalization of the naphthol compound with the ketone compound is, preferably, conducted by using benzene, toluene or xylene as the reaction solvent while removing the formed water out of the system, the reaction temperature being maintained to be not lower than 70° C.

Further, the naphthol derivatives of the general formula (1-1b) are halogenated in a solvent that contains acetonitrile and/or toluene. The preferred halogenating agent is a succinimide compound such as N-chlorosuccinimide, N-bromosuccinimide or N-iodosuccinimide. Though not specifically limited, the reaction temperature during the halogenation is, preferably, not higher than 30° C. and, more preferably, not higher than 10° C.

In synthesizing the halogenonaphthol derivatives, the naphthol derivatives of the general formula (1-1b) obtained as the intermediate product, too, are the novel compounds.

<Boron-Containing Phenyl Compounds Used for the Synthesis of Phenylnaphthol Derivatives and Their Production>

In the synthesis of phenylnaphthol derivatives of the invention, among the boron-containing phenyl compounds (C-1) used in the synthesizing method C, the compound represented by the following formula (1-2):

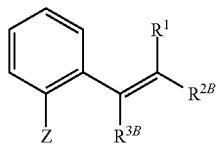
(1-2)

wherein, $R^1$ is a hydrogen atom, an alkyl group or an aryl group, $R^{2B}$ and $R^{3B}$ are as defined in the above-mentioned general formula (1'), and are groups that are bonded together to form an aliphatic hydrocarbon ring or a heterocyclic ring, and the group designated at Z is a boron-containing group selected from the following formulas:

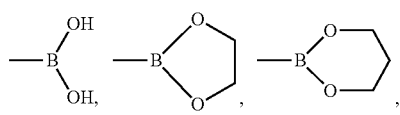

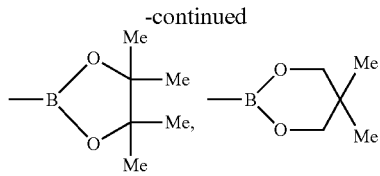

is used for the synthesis of phenylnaphthol derivatives of which the groups $R^1$ and $R^2$ in the general formula (1) are bonded together to form an aliphatic hydrocarbon group or a heterocyclic ring.

Though there is no specific limitation, the boron-containing phenyl compound represented by the formula (1-2) can be synthesized by using, for example, a 2-benzyloxy-1-bromobenzene as the starting material.

That is, the starting material is subjected to the halogen-metal exchange reaction with magnesium or an organo-lithium compound, the obtained reaction product is reacted with a carbonyl compound represented by the following formula:

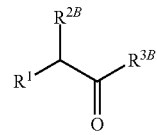

the benzyl group in the obtained compound is removed through the hydrogenation reaction to form a tertiary alcohol which is then subjected to the dehydration reaction with a suitable acid to thereby synthesize a phenol compound represented by the following formula:

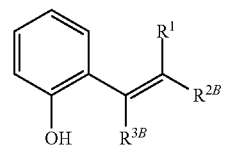

Next, the phenol compound is triflated with the trifluoromethanesulfonic acid, and is reacted with a corresponding boron compound in the presence of a palladium catalyst to obtain the boron-containing phenyl compound represented by the above formula (1-2).

As the palladium catalyst used for the above reaction, there is used the one used for the Suzuki-Miyaura coupling reaction mentioned above. As the boron compound, it is desired to use a boron compound or a diboron compound as concretely represented by 4,4,5,5-tetramethyl-1,3,2-dioxaborane, bis(pinacolato) diboron or bis(neopentyl glycolato) diboron.

The boron-containing phenyl compound represented by the formula (1-2) is favorably used for the synthesizing method C that uses the halogenonaphtol derivative represented by the general formula (1-1a) as the starting material. It is then allowed to synthesize phenylnaphthol derivatives of the invention represented, specifically, by the following general formula (1"):

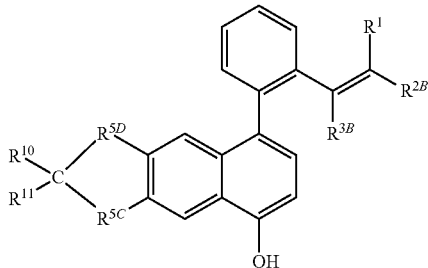
(1")

wherein,

R[1] is a hydrogen atom, an alkyl group or an aryl group,

R[10] and R[11] arehydrogen atoms, alkyl groups, cycloalkyl groups or aryl groups, R[2B] and R[3B] are groups that are bonded together to form an aliphatic hydrocarbon ring or a heterocyclic ring, and R[5C] and R[5D] are oxygen atoms or sulfur atoms provided either one of them is the sulfur atom.

<Production of Indenonaphthol Compounds>

The phenylnaphthol derivatives of the invention represented by the above general formula (1) are used for the synthesis of indenonaphthol compounds represented by the following general formula (2):

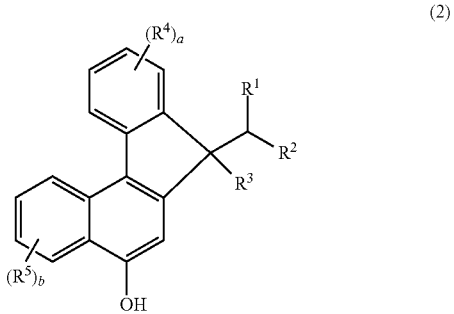

(2)

wherein R[1] to R[5], a and b are as defined in the formula (1).

That is, upon cyclizing the phenylnaphthol derivatives of the invention in the presence of an acid catalyst, there are obtained the indenonaphthol derivatives represented by the above general formula (2) in high yields suppressing the formation of impurities.

As the acid catalyst used for the reaction, there is preferably used an acidic substance that works as the Lewis' acid. Concretely, there can be exemplified sulfuric acid, benzenesulfonic acid, p-toluenesulfonic acid (monohydrate), camphorsulfonic acid and methanesulfonic acid. The amount of the acid that is used should be suitably determined within a range of 0.01 to 10 mols per mole of the phenylnaphthol derivative. From the standpoint of suppressing the formation of by-products, however, the amount of the acid is better small and, for instance, is in a range of 0.1 to 1 mole per mole of the phenylnaphthol derivative.

As the reaction solvent, further, there is preferably used a non-protonic organic solvent such as N-methylpyrrolidone, dimethylformamide, tetrahydrofurane, benzene or toluene.

The reaction temperature is preferably 40 to 80° C. from the standpoint of maintaining a suitable degree of reaction rate yet suppressing the formation of by-products.

The reaction time differs depending on the amount of the acid that is used and the reaction temperature, but is, usually, from 1 to 5 hours.

As described already, the phenylnaphthol derivative of the present invention can be used for the above cyclization reaction by introducing the above-mentioned protection group Ra into the hydroxyl group. Here, the above method permits the protection group Ra to be removed simultaneously with the cyclization. In order to further improve the yield and the purity, however, the protection group Ra is better not introduced. Therefore, if the phenylnaphthol derivative of the invention is produced in a state where the protection group Ra has been introduced, it is desired that the naphthol derivative is used for the above cyclization reaction after having removed the protection group Ra therefrom. Specifically, if the benzyl group or the p-methoxybenzyl group has been introduced as the protection group Ra, it is probable that by-products may form due to the dislocation of the protection group Ra. To suppress the formation of such by-products, therefore, it is desired to first carry out the reaction for removing the protection group based on the reduction with acid, alkali or hydrogen.

As described above, use of the phenylnaphthol derivative of the present invention makes it easy to obtain the indenonaphthol compounds in high yield and in high purity. However, such advantages of the invention are not achieved if the conventional phenylnaphthol compounds are used.

For example, if the conventional phenylnaphthol compound is used while using the p-toluenesulfonic acid as the acid and the toluene as the reaction solvent, then the p-toluenesulfonic acid must be used in an amount in excess of 1 mole per mole of the phenylnaphthol compound, and the reaction temperature must be as high as not lower than 100° C. Therefore, by-products tend to be easily formed, and a high yield cannot be attained. However, if the novel phenylnaphthol derivative of the invention is used, the acid may be used in an amount of not more than 1 mole as described above and the reaction temperature, too, may be lowered to be 40 to 80° C. Namely, the reaction can be carried out under considerably mild conditions suppressing the formation of by-products and, therefore, making it possible to obtain indenonaphthol compounds in high yields.

There is no specific limitation on the method of refining the indenonaphthol compounds obtained as described above, and there can be employed, for example, the silica-gel column refining method or the recrystallization method.

The obtained indenonaphthol compounds are used for the synthesis of indenonaphthopyran derivatives having good photochromic properties.

<Production of Indenonaphthopyran Derivatives>

According to the invention, the indenonaphthopyran compound represented by the following general formula (3) that is useful as a photochromic compound can be produced by using the indenonaphthol compound of the general formula (2) obtained above.

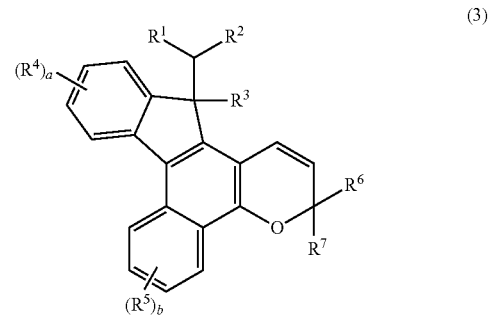

(3)

wherein,

R[1], R[2], R[3], R[4], R[5], a and b are as defined in the above formula (1), and R[6] and R[7] are, respectively, alkyl groups, cycloalkyl groups, aryl groups or heteroaryl groups.

That is, the above indenonaphthol compound can be obtained by reacting the indenonaphthol compound of the general formula (2) with the indenonaphthol compound of the following general formula (4):

(4)

wherein R[6] and R[7] are as defined in the above formula (3).

The above reaction can be conducted in the same manner as the conventional reaction that uses the propargyl alcohol.

For instance, the ratio of the amount (feeding ratio) of the indenonaphthol compound and the propargyl alcohol compound can be selected from a wide range but is, usually, selected from a range of 1:10 to 10:1 (mole ratio).

Further, the reaction is, usually, conducted in the presence of an acid catalyst. As the acid catalyst, there can be used sulfuric acid, benzenesulfonic acid, p-toluenesulfonic acid, camphorsulfonic acid, methanesulfonic acid or pyridinium p-toluenesulfonate in an amount of 0.001 to 1 mole equivalent per mole of the indenonaphthol derivative.

It is, further, allowable to use a solid acid catalyst such as silica gel or acid alumina in an amount of, usually, 0.1 to 10 parts by weight per the sum of 100 parts by weight of the indenonaphthol compound and the propargyl alcohol compound.

The reaction temperature is preferably 0 to 200° C. and the reaction solvent is preferably a non-protonic organic solvent, such as N-methylpyrrolidone, dimethylformamide, tetrahydrofuran, benzene or toluene.

There is no specific limitation, either, on the method of refining the reaction products. For example, the silica-gel column refining is conducted followed by the recrystallization to obtain the indenonapthopyran compounds in high purity and in high yields.

EXAMPLES

The invention will now be described in further detail by way of Examples to which only, however, the invention is in no way limited.

Example 1

Synthesis of the Phenylnaphthol Derivatives Represented By the Following Formula (E1);

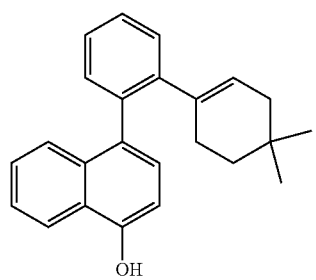

(E1)

22.3 Grams (100 mmols) of 4-bromo-1-naphthol was dissolved in 440 ml of dimethylformamide, and to which 20.7 g (150 mmols) potassium carbonate and 13.9 g (110 mmols) of benzyl chloride were added to react them at 50° C.

After 3 hours have passed, 440 ml of toluene and 880 ml of water were added thereto, the organic layer was washed with water, the solvent was removed and, thereafter, the reaction product was refined by chromatography (solvent chloroform) using silica gel to obtain a white solid material of a 1-benzyloxy-4-bromonaphthalene represented by the following formula in an amount of 29.4 g (94 mmols, yield: 94%).

In the following formula, Bn is a benzyl group which is the protection group (hereinafter the same).

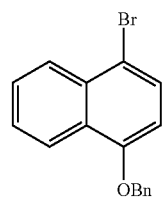 [SMILES: Brc1ccc(OCc2ccccc2)c2ccccc12]

29.4 Grams of the white solid material of the 1-benzyloxy-4-bromonaphthalene obtained above was dissolved in 500 ml of tetrahydrofurane which was then cooled down to −78° C. Thereafter, 70 ml of a butyl lithium hexane solution (1.6 M) was added thereto over a period of one hour.

Next, 23.0 g (122 mmols) of triisopropyl borate was added thereto and the temperature was raised up to 10° C. After one hour has passed, 200 ml of 10% hydrochloric acid was added, the organic layer was washed with 300 ml of 10% brine, the solvent was removed and, thereafter, 300 ml of hexane was added thereto to obtain a white solid material of a boronic acid compound represented by the following formula in an amount of 23.0 g (83 mmols, yield: 88%),

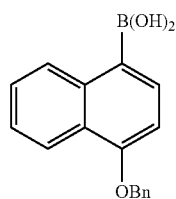 [SMILES: OB(O)c1ccc(OCc2ccccc2)c2ccccc12]

To 23.0 g of the above boronic acid compound, there were added:

Toluene, 200 ml,

Ethanol, 200 ml,

1-Bromo-2-iodobenzene, 25.7 g (91 mmols), and

10% sodium carbonate aqueous solution, 100 ml, and an argon gas was introduced into the reaction solution to remove oxygen dissolved therein.

Next, 4.8 g (4.1 mmols) of a tetrakistriphenylphosphine palladium was added to conduct the reaction at a refluxing temperature for 8 hours. Thereafter, the solvent was removed under reduced pressure, and the reaction product was refined by chromatography (solvent chloroform) using silica gel to obtain a pale yellow solid material of a bromophenylnaphthol compound represented by the following formula in an amount of 26.1 g (67 mmols, yield: 81%).

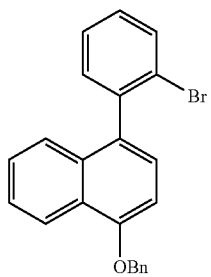 [SMILES: Brc1ccccc1-c1ccc(OCc2ccccc2)c2ccccc12]

26.1 Grams of the bromophenylnaphthol compound was dissolved in 500 ml of tetrahydrofuran which was then cooled down to −78° C., and to which 46 ml of a butyl lithium hexane solution (1.6M) was added over a period of one hour. Thereafter, 10.1 g (80 mmols) of 4,4-dimethylcyclohexanone was added thereto, and the temperature was raised up to 20° C. After one hour has passed, 300 ml of 5% ammonium chloride aqueous solution was added, and 2.54 g (13.4 mmols) of a p-toluenesulfonic acid monohydrate was added to the organic layer to conduct the reaction at 50° C. After 5 hours have passed, 10% brine was added to wash the organic layer.

The solvent was removed from the organic layer which was then refined by chromatography (solvent hexane/ethyl acetate=4/1 v/v) using silica gel to obtain a benzyl-protected phenylnaphthol derivative represented by the following formula in an amount of 21.0 g (50.4 mmols).

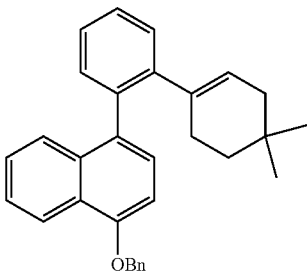 [SMILES: CC1(C)CC=C(c2ccccc2-c2ccc(OCc3ccccc3)c3ccccc23)CC1]

Described below are elementally analyzed values of the phenylnaphthol derivative of which the hydroxyl group is protected with the benzyl group, and calculated values of $C_{31}H_{30}O$.

Elementally analyzed values C: 87.91%, H: 7.27%
Calculated values C: 88.95%, H: 7.22%

The above results tell that the elementally analyzed values are in good agreement with the calculated values of $C_{31}H_{30}O$.

21.0 g of the above phenylnaphthol compound was dissolved in 210 ml of tetrahydrofuran, and 5.2 g of 5% palladium carbon (containing 50 wt of water) was added thereto to conduct the reaction in a hydrogen atmosphere. After 2 hours have passed, the solid material was separated by filtration, the solvent was removed, and the reaction product was refined by chromatography (solvent hexane/ethyl acetate=2/1 v/v) using silica gel to obtain 16.0 g (48.9 mmols) of the phenylnaphthol derivative of the present invention represented by the above formula (E1) from which the benzyl group that is the protection group has been removed.

The total yield of the phenylnaphthol derivative thus obtained from the 4-bromo-1-naphthol was 49%.

Described below are elementally analyzed values of the phenylnaphthol derivative, and calculated values of $C_{24}H_{24}O$.

Elementally analyzed values C: 87.81%, H: 7.30%
Calculated values C: 87.76%, H: 7.37%

The above results tell that the elementally analyzed values are in good agreement with the calculated values of $C_{24}H_{24}O$.

Measurement of the proton nuclear magnetic resonance spectra showed peaks of 12H based on the alkyl group and alkylene group near δ 0.5 to 4.0 ppm, and peaks of 11H based on the aromatic and olefin near δ 5.0 to δ 9.0 ppm.

Further, measurement of the $^{13}C$ nuclear magnetic resonance spectra showed peaks based on the carbon atoms of the aromatic ring near δ 110 to 160 ppm and peaks based on the carbon atoms of the alkyl group and alkylene group at δ 20 to 80 ppm.

From the above analytical results, it was confirmed that the obtained phenylnaphthol derivatives had the structure represented by the formula (E1).

Example 2

Synthesis of the Phenylnaphthol Derivatives Represented By the Following Formula (E2);

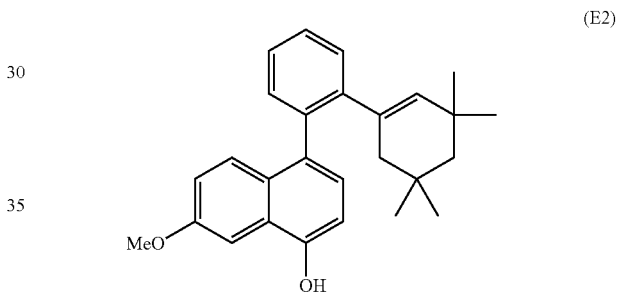

17.4 Grams (100 mmols) of 7-methoxy-1-naphthol was dissolved in 340 ml of acetonitrile, and 17.8 g of N-bromosuccinimide was added thereto at 0° C. to react them. After 2 hours have passed, water and ethyl acetate were added thereto each in an amount of 340 ml. The organic layer was washed with 10% brine, the solvent was removed, and the reaction product was refined by chromatography (solvent chloroform) using silica gel to obtain a pale yellow oil of a bromonaphthol represented by the following formula in an amount of 23.3 g (92 mmols, yield: 92%).

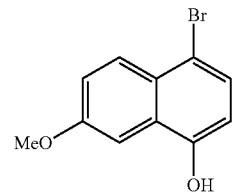 [SMILES: COc1ccc2c(Br)ccc(O)c2c1]

The bromonaphthol was dissolved in 460 ml of dimethylformamide, and to which 19.1 g (138 mmols) of potassium carbonate and 12.8 g (101 mmols) of benzyl chloride were added to conduct the reaction at 50° C. After 3 hours have passed, 460 ml of toluene and 920 ml of water were added, the organic layer was washed with water, the solvent was removed, and the reaction product was refined by chromatography (solvent chloroform) using silica gel to obtain a white solid material of a benzyl-protected bromonaphthol represented by the following formula of which the hydroxyl group is protected with the benzyl group (Bn) in an amount of 29.8 g (87 mmols, yield: 95%).

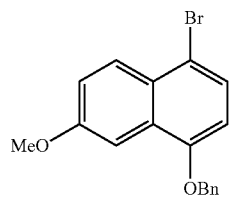 [SMILES: COc1ccc2c(Br)ccc(OCc3ccccc3)c2c1]

To 10.3 g (30 mmols) of the above benzyl-protected bromonaphthol, there were added:
Dimethylformamide, 150 ml,
10% Potassium carbonate aqueous solution, 150 ml, and
2-Bromophenylboronic acid, 9.0 g (45 mmols), and to the reaction solution was introduced an argon gas to remove oxygen dissolved therein. 3.45 Grams (3.0 mmols) of tetrakistriphenylphosphine palladium was added thereto to conduct the reaction at 80° C. for 24 hours. Thereafter, 300 ml of toluene and 300 ml of water were added, the organic layer was washed with water, the solvent was removed under reduced pressure, and the reaction product was refined by chromatography (solvent chloroform) using silica gel to obtain a white solid material of a benzyl-protected bromophenylnaphthol derivative represented by the following formula in an amount of 7.10 g (17 mmols, yield: 57%).

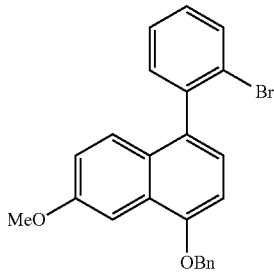 [SMILES: COc1ccc2c(-c3ccccc3Br)ccc(OCc3ccccc3)c2c1]

5.45 Grams (14.1 mmols) of a white solid material of the phenylnaphthol derivative represented by the above-mentioned formula (E2) was obtained by conducting the coupling and the removal of protection in the same manner as in Example 1 but using the above benzyl-protected bromophenylnaphthol derivative and a 3,3,5,5-tetramethylcyclohexanone instead of using the 4,4-dimethylcyclohexanone.

The total yield from the 7-methoxy-1-naphthol was 41%.

The obtained compound was analyzed for its structure relying on the same means for confirming the structure as that of Example 1, and was confirmed to be the compound represented by the above formula (E2). Table 1 shows elementally analyzed values and characteristic spectra in the $^1$H-NMR spectra.

Example 3

Synthesis of Phenylnaphthol Derivatives Represented By the Following Formula (E3);

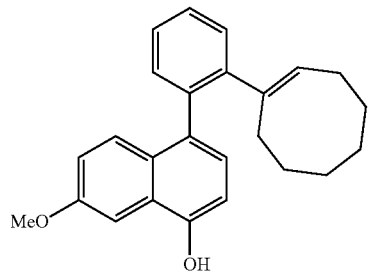

526 Milliliters of toluene was added to 26.3 g (100 mmols) of 1-benzyloxy-2-bromobenzene, cooled down to −10° C., and 75 ml of a butyl lithium hexane solution (1.6 M) was added thereto over a period of one hour.

263 Milliliters of water was added to the reaction solution, and the organic layer was washed with water. The solvent was removed, 465 ml of ethyl acetate and 62 ml of methanol were added thereto, and 5.2 g of 5% palladium carbon (containing 50 wt of water) was added to conduct the reaction in a hydrogen atmosphere.

After 2 hours have passed, the solid material was separated by filtering, the solvent was removed, and the reaction product was refined by chromatography (solvent hexane/ethyl acetate=5/1 v/v) using silica gel to obtain 9.91 g (45 mmols) of a phenol compound represented by the following formula.

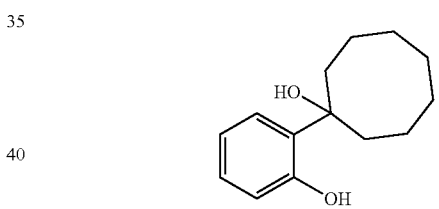

200 Milliliters of toluene and 2.1 g (9.0 mmols) of camphorsulfonic acid were added to the phenol compound to conduct the reaction at 80° C. After 2 hours have passed, 200 ml of water was added, the organic layer was washed with water, and the solvent was removed.

137 Milliliters of dichloromethane and 10.9 ml of pyridine were added to the residual transparent oil from which the solvent has been removed, and the mixture was cooled down to −10° C. 19.0 Grams (67.5 mmols) of trifluoromethanesulfonic anhydride was added thereto dropwise over a period of one hour. Thereafter, the mixture was reacted and matured at 0° C. for one hour, 137 ml of water was added thereto, the dichloromethane phase was separated, 45 ml of 10% hydrochloric acid was added, and the aqueous layer was removed to thereby remove the pyridine.

Next, the dichloromethane phase was washed with water, the solvent was removed, and the reaction product was refined by chromatography (solvent chloroform) using silica gel to obtain 13.5 g (40.5 mmols) of a triflate compound represented by the following formula.

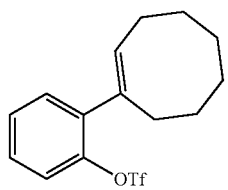 [SMILES: O=S(=O)(Oc1ccccc1/C1=C/CCCCCC1)C(F)(F)F]

The triflate compound was dissolved in 203 ml of dimethyl sulfoxide and to which were added:

Bis(pinacolato) diboron, 15.4 g (60.8 mmols),
Potassium acetate, 13.9 g (141 mmols), and
Tetrakistriphenylphosphine palladium, 3.45 g (3.0 mmols), to conduct the reaction at 80° C. for 16 hours. 203 Milliliters of toluene and 203 ml of water were added to the reaction solution, the organic layer was washed with water, the solvent was removed, and the reaction product was refined by chromatography (solvent chloroform) using silica gel to obtain 11.0 g (35.2 mmols) of a white solid material of boronic acid ester compound represented by the following formula.

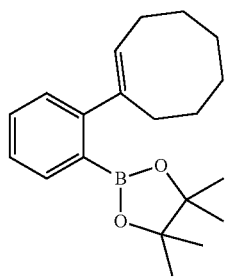 [SMILES: CC1(C)OB(c2ccccc2/C2=C/CCCCCC2)OC1(C)C]

Described below are elementally analyzed values of the white solid material and values calculated from the above formula.

Elementally analyzed values C: 76.88%, H: 9.40%, B: 3.51%

Calculated values C: 76.93%, H: 9.36%, B: 3.46%

It will be learned that the elementally analyzed values and the calculated values are in good agreement.

Boronic acid ester obtained above, 9.37 g (30 mmols),
Benzyl-protected bromophenylnaphthol derivative obtained in Example 2, 6.87 g (20 mmols),
1,2-Dimethoxyethane, 200 ml,
Ethanol, 20 ml, and
10% Sodium carbonate aqueous solution, 200 ml, were mixed together, and to which an argon gas was introduced to remove oxygen dissolved therein. To the mixture was added 3.45 g (3.0 mmols) of tetrakistriphenylphosphine palladium to conduct the reaction at 75° C. for 24 hours.

Thereafter, 200 ml of toluene and 200 ml of water were added thereto, the organic layer was washed with water, the solvent was removed under reduced pressure, and the reaction product was refined by chromatography (solvent chloroform) using silica gel to obtain 7.90 g (17.6 mmols) of a white solid material of a benzyl-protected phenylnaphthol derivative represented by the following formula.

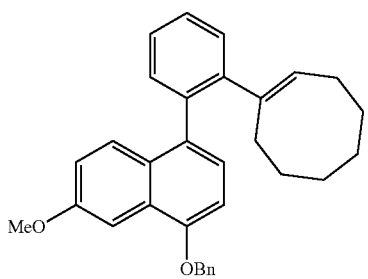 [SMILES: COc1ccc2c(-c3ccccc3/C3=C/CCCCCC3)ccc(OCc3ccccc3)c2c1]

The phenylnaphthalene compound was dissolved in 160 ml of tetrahydrofurane, and 3.95 g of 5% palladium carbon (containing 50 wt of water) was added thereto to conduct the reaction in a hydrogen atmosphere. After 2 hours have passed, the solid material was separated by filtration, the solvent was removed, and the reaction product was refined by chromatography (solvent chloroform) using silica gel to obtain 6.02 g (16.8 mmols) of a white solid material of the phenylnaphthol derivative of the above formula (E3).

The total yield from the 7-methoxy-1-naphthol was 73%.

The obtained compound was analyzed for its structure relying on the same means for confirming the structure as that of Example 1, and was confirmed to be the compound represented by the above formula. Table 1 shows elementally analyzed values and characteristic spectra in the $^1$H-NMR spectra.

Example 4

Synthesis of Indenonaphthol Derivatives;

58 Milliliters of toluene was added to 3.87 g (10 mmols) of the phenylnaphthol derivative of the formula (E2) obtained in Example 2, and the mixture was heated at 80° C. 0.95 Grams (5.0 mmols) of a p-toluenesulfonic acid monohydrate was added thereto to conduct the reaction for 2 hours. After the reaction, the organic layer was washed with 30 ml of water, the solvent was removed, and the reaction product was refined by chromatography (solvent chloroform) using silica gel to obtain 3.75 g (9.7 mmols) of a white solid material of an indenonaphthol derivative represented by the following formula (E4).

The yield from the phenylnaphthol derivative was 97%.

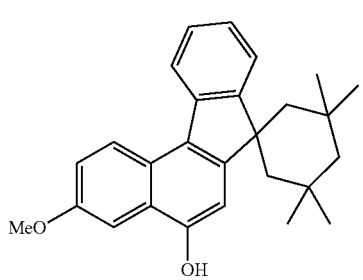

(E4)

Example 5

Synthesis of Indenonaphthopyrans;

A propargyl alcohol compound represented by the following formula was provided.

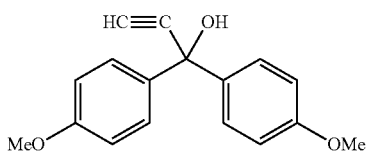 [SMILES: C#CC(O)(c1ccc(OC)cc1)c1ccc(OC)cc1]

1.55 Grams (4.0 mmols) of the indenonaphthol compound obtained in Example 4 and 1.40 g (5.2 mmols) of the above propargyl alcohol compound were dissolved in 47 ml of toluene and to which was, further, added 0.03 g of camphorsulfonic acid to conduct the reaction at 100° C. for one hour.

After the reaction, the solvent was removed, the reaction product was refined by chromatography (solvent chloroform) using silica gel and was, further, recrystallized with acetonitrile to obtain 1.86 g (2.9 mmols) of a white solid material of an indenonaphthopyran represented by the following formula (E5). The yield was 73%.

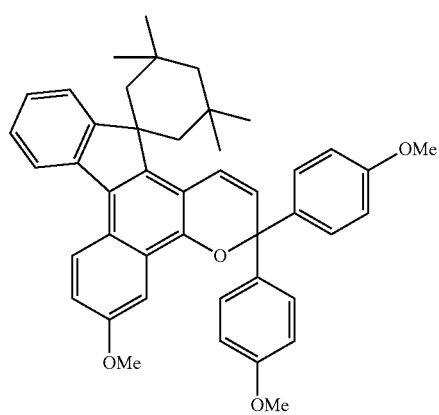

(E5)

Example 6

Synthesis of Phenylnaphthol Derivatives Represented By the Following Formula (E6).

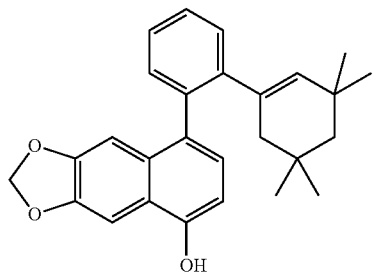

(E6)

A 6,7-methylenedioxy-1-naphthol represented by the following formula was provided.

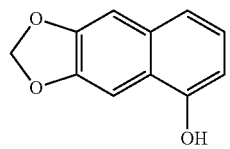 [SMILES: Oc1cccc2cc3c(cc12)OCO3]

The phenylnaphthol derivatives represented by the above formula (E6) were obtained by the same method as in Example 2 but using the above 6,7-methylenedioxy-1-naphthol as the starting material (yield, 390).

The obtained compound was analyzed for its structure relying on the same means for confirming the structure as that of Example 1, and was confirmed to be the compound represented by the above formula (E6). Table 1 shows elementally analyzed values and characteristic spectra in the $^1$H-NMR spectra.

Example 7

Synthesis of Phenylnaphthol Derivatives Represented By the Following Formula (E7); Example 7.

18.8 Grams (100 mmols) of 1,6-dimethoxynaphthalene was dissolved in 370 ml of tetrahydrofuran which was then cooled down to −10° C., and 78 ml of a butyl lithium hexane solution (1.6 M) was added thereto over a period of one hour. To the solution was added 3.2 g (100 mmols) of the flower of sulfur little by little to conduct the reaction at −5° C. for 3 hours. To the solution was added 370 ml of toluene, the mixture was quenched with 190 ml of 10% hydrochloric acid, and the organic layer was washed with 10% brine. The solvent was removed, and the reaction product was refined by chromatography (solvent hexane/ethyl acetate=3/1 v/v) using silica gel to obtain 15.4 g (70 mmols) of a pale yellow oil of a naphthol derivative represented by the following formula.

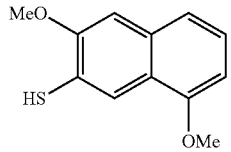 [SMILES: COc1cc2cccc(OC)c2cc1S]

To 15.4 g of the thus obtained naphthol derivative was added 154 ml of dichloromethane, and the mixture was cooled down to 0° C. 217 Grams of a dichloromethane triborate solution (17 wt %) was added thereto over a period of one hour to conduct the reaction for 3 hours.

The solution was quenched by adding 154 ml of water thereto followed by the addition of 308 ml of ethyl acetate, the aqueous layer was removed, the organic layer was washed with water, and the solvent was removed to obtain a dinahthol compound represented by the following formula.

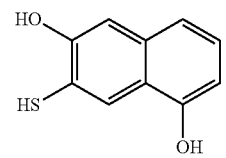

The dinaphthol compound that is subject to be decomposed with oxygen was not refined but was used for the next reaction. Further, the water used in the step of synthesizing the dinaphthol was the one from which oxygen dissolved therein had been removed in advance by bubbling with the argon gas.

To the above dinaphthol compound, there were added 412 ml of toluene, 8.00 g (77 mmols) of diisopropyl ketone and 1.33 g (5.0 mmols) of p-toluenesulfonic acid monohydrate to conduct the reaction at a refluxing temperature for 16 hours while removing water that was formed. After the reaction, the organic layer was washed with water, the solvent was removed, and the reaction product was refined by chromatography (solvent hexane/ethyl acetate=2/1 v/v) using silica gel to obtain 11.7 g (41 mmols) of a pale yellow viscous oil of a naphthol compound represented by the following formula.

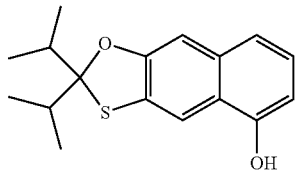 [SMILES: CC(C)C1(C(C)C)Oc2cc3cccc(O)c3cc2S1]

Elementally analyzed values and calculated values of the compound were as follows:

Elementally analyzed values C: 70.69%, H: 7.10%, S: 11.16%

Calculated values C: 70.80%, H: 6.99%, S: 11.12%

It will be understood that the elementally analyzed values and the calculated values are in good agreement.

The naphthol compound obtained above was brominated and benzyl-etherified (introduction of a protection group) in the same manner as in Example 2 to obtain 12.3 g (27 mmols, yield: 66%) of a white solid material of a benzyl-protected bromonaphthol compound represented by the following formula.

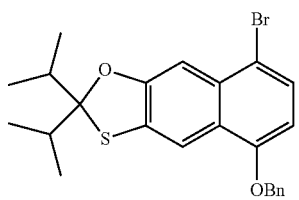 [SMILES: CC(C)C1(C(C)C)Oc2cc3c(Br)ccc(OCc4ccccc4)c3cc2S1]

Elementally analyzed values and calculated values of the compound were as follows:

Elementally analyzed values C: 62.89%, H: 5.47%, S: 7.09%

Calculated values C: 63.02%, H: 5.51%, S: 7.01%

It will be understood that the elementally analyzed values and the calculated values are in good agreement.

On the other hand, a boronic acid ester compound represented by the following formula was obtained in the same manner as in Example 3 but using the 4,4-diethylcyclohexanone instead of the cyclooctanone.

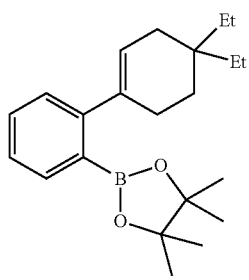 [SMILES: CCC1(CC)CC=C(c2ccccc2B2OC(C)(C)C(C)(C)O2)CC1]

Elementally analyzed values and calculated values of the compound were as follows:

Elementally analyzed values C: 77.55%, H: 9.59%, B: 3.22%

Calculated values C: 77.65%, H: 9.77%, B: 3.18%

It will be understood that the elementally analyzed values and the calculated values are in good agreement.

The total yield of the boronic acid ester compound from the 1-benzyloxy-2-bromobenzene was 53%.

The benzyl-protected bromonaphthol compound and the boronic acid ester compound obtained above were reacted together in the same manner as in Example 3 to obtain the phenylnaphthol derivative represented by the above formula (E7). The total yield of the phenylnaphthol derivative from the naphthol compound was 68%.

The obtained compound was analyzed for its structure relying on the same means as that of Example 1 and was confirmed to be the compound represented by the above formula (E7). Table 1 shows the elementally analyzed values and characteristic spectra in the $^1$H-NMR spectra.

Example 8

Synthesis of Phenylnaphthol Derivatives Represented by the Following Formula (E8).

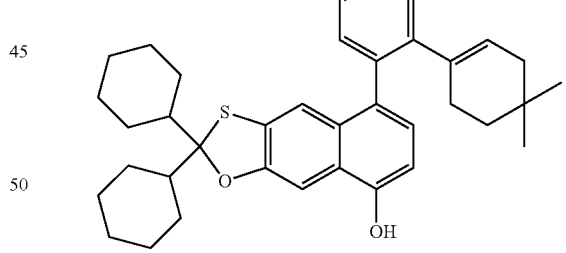

Phenylnaphthol derivatives represented by the above formula (E8) were obtained in the same manner as in Example 7 but using the 1, 7-dimethoxynaphthalene as the starting material, using the dicyclohexyl ketone instead of the diisopropyl ketone, and using the 4,4-dimethylcyclohexanone instead of the 4,4-diethylcyclohexanone. The total yield of the phenylnaphthol derivatives from the naphthol compound was 70%.

The obtained compound was analyzed for its structure relying on the same means as that of Example 1 and was confirmed to be the compound represented by the above formula (E8). Table 1 shows the elementally analyzed values and characteristic spectra in the $^1$H-NMR spectra.

Example 9

Synthesis of Phenylnaphthol Derivatives Represented by the Following Formula (E9).

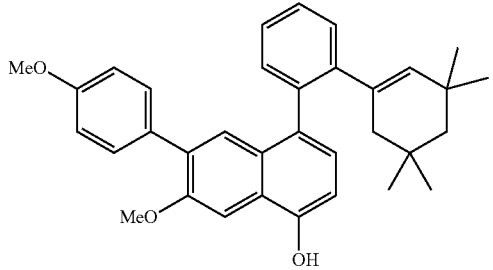 [SMILES: COc1ccc(-c2cc3c(-c4ccccc4C4=CC(C)(C)CC(C)(C)C4)ccc(O)c3cc2OC)cc1]

17.4 Grams (100 mmols) of the 7-methoxy-1-naphthol was protected with benzyl in the same manner as in Example 1 to obtain 24.6 g (93 mmols) of a white solid material of a 1-benzyloxy-7-methoxynaphthalene represented by the following formula.

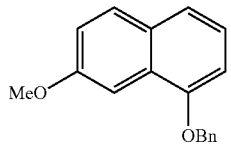 [SMILES: COc1ccc2cccc(OCc3ccccc3)c2c1]

The 1-benzyloxy-7-methoxynaphthalene was lithiated in the same manner as in Example 7, and to which 1,2-dibromoethane was added instead of adding the flower of sulfur. There was obtained a pale yellow solid material of a 1-benzyloxy-6-bromo-7-methoxynaphthalene represented by the following formula in an amount of 18.1 g (53 mmols, yield: 57%).

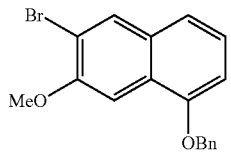 [SMILES: COc1cc2c(OCc3ccccc3)cccc2cc1Br]

The compound was dissolved in 360 ml of dimethoxyethane followed by the addition of 36 ml of ethanol and 400 ml of 10% sodium carbonate aqueous solution, and to which an argon gas was introduced to remove oxygen dissolved therein.

To the solution, there were added:

4-Methoxyphenylboronic acid, 8.86 g (58 mmols), and

Tetrakistriphenylphosphine palladium, 0.67 g (0.58 mmols), to conduct the reaction at 75° C. for 3 hours. Thereafter, 360 ml of toluene and 360 ml of water were added thereto, the organic layer was washed with water, the solvent was removed under reduced pressure, and the reaction product was refined by chromatography (solvent chloroform) using silica gel to obtain 18.8 g (51 mmols, yield: 96%) of a white solid material of a 1-benzyloxy-6-(4-methoxyphenyl)-7-methoxynaphthalene represented by the following formula.

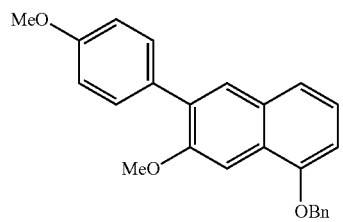 [SMILES: COc1ccc(-c2cc3cccc(OCc4ccccc4)c3cc2OC)cc1]

The compound was brominated in the same manner as in Example 2 to obtain 14.3 g (32 mmols, yield: 63%) of a pale yellow solid material of a benzyl-protected bromonaphthol compound represented by the following formula.

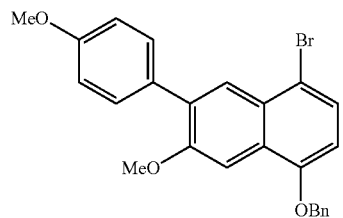 [SMILES: COc1ccc(-c2cc3c(Br)ccc(OCc4ccccc4)c3cc2OC)cc1]

The above benzyl-protected bromonaphthol compound was reacted with the triisopropyl borate in the same manner as in Example 1 to obtain 12.1 g (29 mmols, yield: 91%) of a white solid material of a boronic acid compound represented by the following formula.

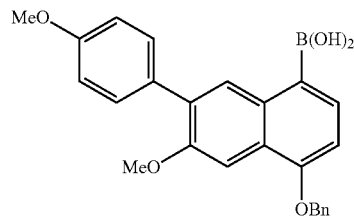 [SMILES: COc1ccc(-c2cc3c(B(O)O)ccc(OCc4ccccc4)c3cc2OC)cc1]

The boronic acid compound was reacted with the 3,3,5,5-tetramethylcyclohexanone instead of with the 4,4-dimethylcyclohexanone in the same manner as in Example 1 to obtain the phenylnaphthol derivatives represented by the above formula (E9). The total yield of the phenylnaphthol derivatives from the 7-methoxy-1-naphthol was 19%.

The obtained compound was analyzed for its structure relying on the same means as that of Example 1 and was confirmed to be the compound represented by the above formula (E9). Table 1 shows the elementally analyzed values and characteristic spectra in the $^1$H-NMR spectra.

TABLE 1

| Ex. No. | Elementally analyzed values | | | | | | $^1$H-NMR (NMR) |
|---|---|---|---|---|---|---|---|
| | Found | | | Calculated | | | |
| | C | H | S | C | H | S | |
| 1 | 87.81 | 7.30 | | 87.76 | 7.37 | | δ5.0–9.0 11H |
| | | | | | | | δ0.5–4.0 12H |
| 2 | 83.96 | 7.69 | | 83.90 | 7.82 | | δ5.0–9.0 10H |
| | | | | | | | δ0.5–4.0 19H |
| 3 | 83.70 | 7.37 | | 83.76 | 7.31 | | δ5.0–9.0 10H |
| | | | | | | | δ0.5–4.0 15H |

TABLE 1-continued

| Ex. No. | Elementally analyzed values | | | | | | ¹H-NMR (NMR) |
|---|---|---|---|---|---|---|---|
| | Found | | | Calculated | | | |
| | C | H | S | C | H | S | |
| 6 | 80.85 | 7.08 | | 80.97 | 7.05 | | δ5.0-9.0 9H |
| | | | | | | | δ0.5-4.0 18H |
| 7 | 78.96 | 8.01 | 6.47 | 79.15 | 8.05 | 6.40 | δ5.0-9.0 9H |
| | | | | | | | δ0.5-4.0 30H |
| 8 | 80.51 | 7.87 | 5.84 | 80.39 | 8.02 | 5.80 | δ5.0-9.0 9H |
| | | | | | | | δ0.5-4.0 34H |
| 9 | 83.14 | 7.19 | | 82.89 | 7.37 | | δ5.0-9.0 13H |
| | | | | | | | δ0.5-4.0 22H |

Reference Example 1

This Example synthesizes, relying on a conventional method, the indenonaphthol compound represented by the formula (E4) that was also synthesized in Example 4.

20 Grams (115 mmols) of diethyl succinate and 100 ml of tetrahydrofurane were added to 21.2 g (100 mmols) of 4-methoxybenzophenone, and were homogeneously dissolved therein.

To the solution was added, dropwise and at 50° C., a solution of 125 ml of tetrahydrofurane in which 12.9 g (115 mmols) of potassium-t-butoxide has been dispersed, and the reaction was conducted at 60° C. for 3 hours. After the reaction, 170 ml of water and 125 ml of toluene were added thereto to separate the solution, and the organic layer was washed with 10% brine. The solvent was removed under reduced pressure to obtain a residue containing a carboxylic acid compound represented by the following formula and its structural isomers.

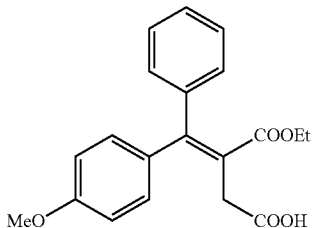 [SMILES: CCOC(=O)/C(CC(=O)O)=C(\c1ccccc1)c1ccc(OC)cc1]

To the residue, there were added:

Acetic anhydride, 51.0 g (500 mmols),

Sodium acetate, 8.2 g (100 mmols), and

Toluene, 100 ml, to conduct the reaction at a refluxing temperature for 3 hours. The reaction solution was cooled down to 20° C., 100 ml of water was added thereto, the mixture thereof was stirred for 3 hours, and the aqueous layer was removed. The solvent was removed under reduced pressure, and the reaction product was recrystallized with 150 ml of methanol to obtain 9.84 g (27 mmols) of a pale yellow solid material of an acetoxynaphthalene compound represented by the following formula.

In the formula, Ac is an acetyl group.

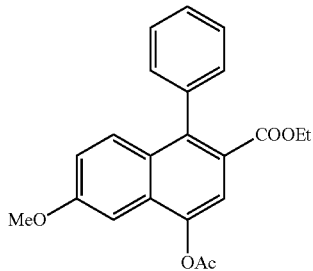 [SMILES: CCOC(=O)c1cc(OC(C)=O)c2cc(OC)ccc2c1-c1ccccc1]

To the pale yellow solid material of the acetoxynaphthalene compound obtained above, there were added 45 ml of methanol and 54 g of 20% sodium hydroxide to react them at a refluxing temperature for 2 hours. Thereafter, 150 ml of toluene and 50 ml of water were added thereto followed by the addition of 30 g of 36% hydrochloric acid so as to be neutralized, and 50 ml of tetrahydrofuran was added thereto to remove the aqueous layer.

Next, the organic layer was washed with 10% brine, the solvent was removed under reduced pressure, and the reaction product was recrystallized with 40 ml of toluene to obtain 7.63 g (25.9 mmols) of a white solid material of a hydroxycarboxylic acid compound represented by the following formula.

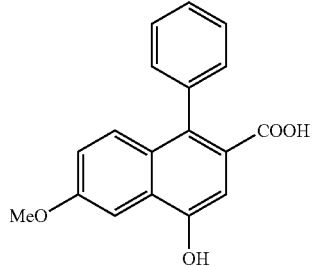 [SMILES: COc1ccc2c(-c3ccccc3)c(C(=O)O)cc(O)c2c1]

The hydroxycarboxylic acid compound obtained above was dissolved in 76 ml of N,N-dimethylformamide, and 9.0 g (64.8 mmols) of potassium carbonate and 7.2 g (57 mmols) of benzyl chloride were added thereto to react them at 60° C. for 4 hours. To the reaction solution, there were added 76 ml of toluene and 114 ml of water. The aqueous layer was removed, the organic layer was washed with water, and the solvent was removed under reduced pressure.

To the residue from which the solvent has been removed, there were added 53 ml of 2-propanol and 104 g of 10% sodium hydroxide aqueous solution to react them at a refluxing temperature for 5 hours so that the solid materials were homogeneously dissolved therein.

After the reaction, the solvent was removed, 55 ml of toluene was added thereto, the mixture thereof was neutralized with 28.9 g of 36% hydrochloric acid, 105 ml of tetrahydrofuran was added thereto to remove the aqueous layer, the organic layer was washed with 10% brine, and the solvent was removed. By recrystallizing the reaction mixture with 200 ml of toluene, there was obtained 9.27 g (24.1 mmols) of a white solid material of a carboxylic acid compound represented by the following formula, the hydroxyl group of which being protected with the benzyl group.

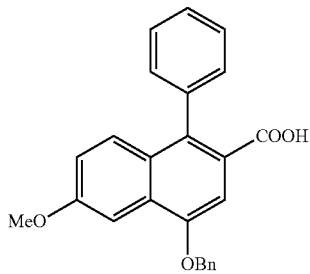 [SMILES: COc1ccc2c(-c3ccccc3)c(C(=O)O)cc(OCc3ccccc3)c2c1]

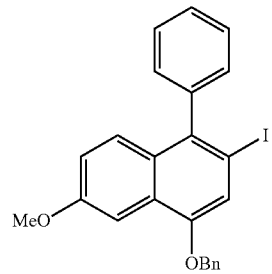

To the carboxylic acid compound obtained above, there were added 93 ml of toluene, 2.68 g (26.5 mmols) trimethylamine and 8.62 g (31.3 mmols) of diphenylphosphoryl azide to react them at 20° C. for 3 hours. Thereafter, 4.0 g of ethanol was added thereto to conduct the urethanation reaction at 70° C. for one hour. Further, 37.7 g of ethanol and 13.5 g of potassium hydroxide were added thereto to conduct the reaction at a refluxing temperature for 3 hours. Thereafter, the solvent was removed, 93 ml of toluene and 62 ml of water were added thereto, the aqueous layer was removed, the organic layer was washed with water, the solvent was removed under reduced pressure, and the reaction product was refined by chromatography (solvent chloroform) using silica gel to obtain 7.54 g (21.2 mmols) of an amine compound represented by the following formula.

The thus obtained iodonaphthalene compound was dissolved in 69 ml of tetrahydrofurane, cooled down to –78° C., and to which 11 ml of a butyl lithium hexane solution (1.6 M) was added over a period of one hour. Thereafter, 2.86 g (18.6 mmols) of 3,3,5,5-tetramethylcyclohexanone was added, and the temperature was raised up to 20° C.

After one hour has passed, 300 ml of a 5% ammonium chloride aqueous solution was added, and 0.56 g (3.0 mmols) of p-toluenesulfonic acid monohydrate was added to conduct the reaction at 50° C. After 5 hours have passed, 10% brine was added thereto to wash the organic layer.

To the organic layer, 1.5 g of 5% palladium carbon (containing 50 wt of water) was added to conduct the reaction in a hydrogen atmosphere. After 2 hours have passed, the solid material was separated by filtration, the solvent was removed, and the reaction product was refined by chromatography (solvent hexane/ethyl acetate=2/1 v/v) using silica gel to obtain 4.17 g (10.8 mmols) of a white solid material of a phenylnaphthol compound represented by the following formula.

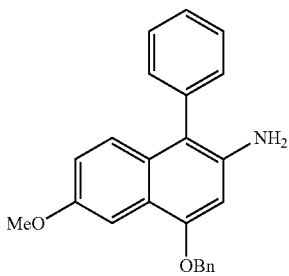 [SMILES: COc1ccc2c(-c3ccccc3)c(N)cc(OCc3ccccc3)c2c1]

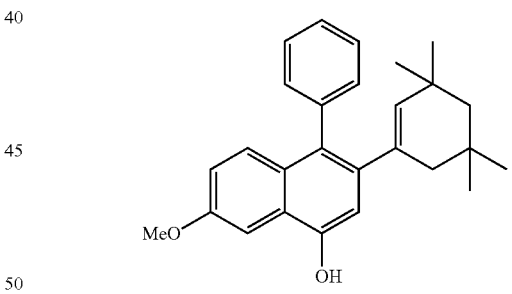

To the thus obtained amine compound, there were added 150 ml of acetonitrile and 42.6 g of 6% hydrochloric acid, followed by the addition of 20% sodium nitrite aqueous solution at 5° C. to diazotize the solution thereof. To the solution, there was added dropwise 35.2 g of a 50% potassium iodide aqueous solution to conduct the reaction at 20° C. for 3 hours.

After the reaction, 115 ml of toluene was added thereto, the aqueous layer was removed, the organic layer was washed with water, the solvent was removed under reduced pressure, and the reaction product was refined by chromatography (solvent chloroform) using silica bel to obtain 6.92 g (14.8 mmols) of a pale yellow solid material of an iodonaphthalene compound represented by the following formula.

The above phenylnaphthol compound was dissolved in 62 ml of toluene and to which 3.09 g (16.3 mmols) of p-toluenesulfonic acid monohydrate was added to conduct the reaction at a refluxing temperature for one hour. After the reaction has been finished, 60 ml of water was added, the aqueous layer was removed, the organic layer was washed with water, the solvent was removed, and the reaction product was refined by chromatography (solvent chloroform) using silica gel to obtain 4.07 g (9.1 mmols) of a white solid material of an indenonaphthol compound represented by the following formula.

The indenonaphthol compound was the same compound as the one synthesized in Example 4.

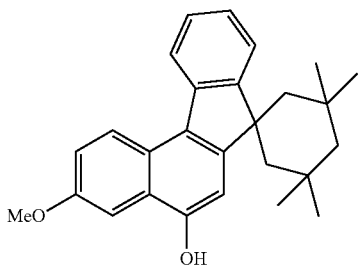 [SMILES: COc1ccc2c3c(cc(O)c2c1)C1(CC(C)(C)CC(C)(C)C1)c1ccccc1-3]

The yield of the indenonaphthol compound from the phenylnaphthol compound was 84%. The total yield thereof from the 4-methoxybenzophenone was as small as 9.1%.

The invention claimed is:

1. Phenylnaphthol derivatives represented by the following general formula (1):

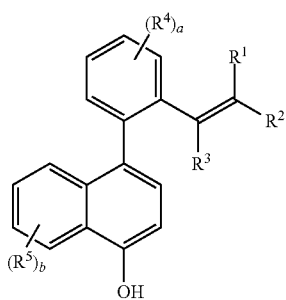

wherein,

R$^1$, R$^2$ and R$^3$ are hydrogen atoms, alkyl groups or aryl groups, and R$^2$ and R$^3$ may be bonded together to form an aliphatic hydrocarbon ring or a heterocyclic ring, a is an integer of 0 to 4, b is an integer of 0 to 4, R$^4$ and R$^5$ are hydroxyl groups, alkyl groups, haloalkyl groups, cycloalkyl groups, alkoxy groups, amino groups, heterocyclic groups having a nitrogen atom as a hetero atom and are bonded together via the nitrogen atom, cyano groups, nitro groups, formyl groups, hydroxycarbonyl groups, alkylcarbonyl groups, alkoxycarbonyl groups, halogen atoms, aralkyl groups, aralkoxy groups, aryloxy groups, aryl groups, heteroaryl groups bonded together via a carbon atom in the ring, alkylthio groups, cycloalkylthio groups, arylthio groups or heteroarylthio groups, and if R$^4$ or R$^5$ are present in a plural number, the plurality of R$^4$ or the plurality of R$^5$ may be the same or different, or 2 R$^4$s or 2 R$^5$s may be bonded together to form an alicyclic hydrocarbon ring or a heterocyclic ring.

2. A process for producing an indenonaphthol compound represented by the following formula (2):

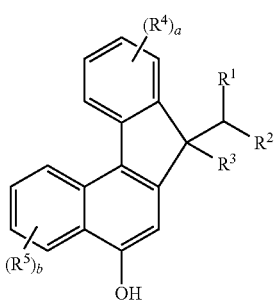

wherein R$^1$, R$^2$, R$^3$, R$^4$, R$^5$, a and b are as defined in the formula (1), by cyclizing the phenylnaphthol derivative of claim 1 in the presence of an acid catalyst.

* * * * *